US011060100B2

(12) United States Patent
Dileo et al.

(10) Patent No.: US 11,060,100 B2
(45) Date of Patent: Jul. 13, 2021

(54) NEMATODE RESISTANCE

(71) Applicant: Keygene N.V., Wageningen (NL)

(72) Inventors: Matthew Vitabile Dileo, Silver Spring, MD (US); Jesse David Munkvold, Rockville, MD (US); Martin De Vos, Wageningen (NL); Anna Maria Tomczak, Wageningen (NL); Sandra Goritschnig, Wageningen (NL)

(73) Assignee: KEYGENE N.V., Wageningen (NL)

( * ) Notice: Subject to any disclaimer, the term of this patent is extended or adjusted under 35 U.S.C. 154(b) by 78 days.

(21) Appl. No.: 16/310,349

(22) PCT Filed: Jun. 16, 2017

(86) PCT No.: PCT/NL2017/050400
§ 371 (c)(1),
(2) Date: Dec. 14, 2018

(87) PCT Pub. No.: WO2017/217852
PCT Pub. Date: Dec. 21, 2017

(65) Prior Publication Data
US 2020/0248195 A1 Aug. 6, 2020

(30) Foreign Application Priority Data

Jun. 16, 2016 (NL) ..................................... 2016980

(51) Int. Cl.
*C12N 15/82* (2006.01)
*C07K 14/41* (2006.01)
*C07K 14/415* (2006.01)

(52) U.S. Cl.
CPC ........ *C12N 15/8216* (2013.01); *C07K 14/415* (2013.01); *C12N 15/8285* (2013.01)

(58) Field of Classification Search
None
See application file for complete search history.

(56) References Cited

FOREIGN PATENT DOCUMENTS

| WO | WO 2008/095972 A1 | 8/2008 |
| WO | WO 2008/139334 A2 | 11/2008 |
| WO | WO 2011/104153 A1 | 9/2011 |

OTHER PUBLICATIONS

The *Arabidopsis* Information Resource page for locus AT4G30935.*
Alonso et al 2003 (Science 301: p. 653-657 plus supplemental) (Year: 2003).*
Grunewald et al., "A Role for AtWRKY23 in Feeding Site Establishment of Plant-Parasitic Nematodes", Plant Physiology, vol. 148, No. 1, Jul. 18, 2008, pp. 358-368.
Amjad Ali et al., "The Beet Cyst Nematode *Heterodera schachtii* Modulates the Expression of WRKY Transcription Factors in Syncytia to Favour Its Development in *Arabidopsis* Roots", PLOS One, vol. 9, No. 7, Jul. 17, 2014, e102360.
Pandey et al., "The Role of WRKY Transcription Factors in Plant Immunity", Plant Physiology, American Society of Plant Physiologists, vol. 150, No. 4, Aug. 1, 2009, pp. 1648-1655.
Grzechowiak et al., "The role of WRKY transcription factors in plants", Biotechnologia, vol. 95, No. 3, 2014, pp. 215-233.
Atamian, "SlWRKY70 is requirement for Mi-1-mediated resistance to aphids and nematode in tomato", Planta, col. 235, No. 2, Sep. 7, 2011, pp. 299-309.
Younis, "RNA Interence (RNAi) Induced Gene Silencing: A Promising Approach of hi-Tech Plant Breeding", International Journal of Biological Sciences, vol. 10, No. 10, Jan. 1, 2014, pp. 1150-1158.
International Search Report issued in PCT/NL2017/050400, dated Sep. 5, 2017.
Written Opinion of the International Searching Authority issued in PCT/NL2017/050400, dated Sep. 5, 2017.
Eulgem et al: "The WRKY superfamily of plant transcription factors", (May 2000), Trends in Plant Science, vol. 5, No. 5, pp. 199-206).
Gheysen et al., "How nematodes manipulate plant development pathways for infection", Current Opinion in Plant Biology, 2011, vol. 14, pp. 415-421 (7 pages).
UnitProtKB—A0A0V0I9Y1 (A0A0V0I9Y1_SOLCH), "Putative WRKY transcription factor 32-like" (5 pages).

* cited by examiner

*Primary Examiner* — Matthew R Keogh
(74) *Attorney, Agent, or Firm* — Foley & Lardner LLP; Sunit Talapatra

(57) ABSTRACT

The invention is in the field of agriculture, in particular in the field of crop protection, more particularly in the field of providing nematode resistance to plants. A method for producing a plant having improved nematode resistance, particularly to root-knot nematodes and/or cyst nematodes, is disclosed, as well as a plant produced by such method.

14 Claims, 3 Drawing Sheets
Specification includes a Sequence Listing.

SEQUENCE LISTING

```
<160> NUMBER OF SEQ ID NOS: 18

<210> SEQ ID NO 1
<211> LENGTH: 511
<212> TYPE: PRT
<213> ORGANISM: Unknown
<220> FEATURE:
<223> OTHER INFORMATION: Description of Unknown:
      Solanaceae sequence
<220> FEATURE:
<221> NAME/KEY: MOD_RES
<222> LOCATION: (21)..(21)
<223> OTHER INFORMATION: Any naturally occurring amino acid
<220> FEATURE:
<221> NAME/KEY: MOD_RES
<222> LOCATION: (191)..(191)
<223> OTHER INFORMATION: Any naturally occurring amino acid
<220> FEATURE:
<221> NAME/KEY: MOD_RES
<222> LOCATION: (265)..(265)
<223> OTHER INFORMATION: Any naturally occurring amino acid
<220> FEATURE:
<221> NAME/KEY: MOD_RES
<222> LOCATION: (287)..(287)
<223> OTHER INFORMATION: Any naturally occurring amino acid
<220> FEATURE:
<221> NAME/KEY: MOD_RES
<222> LOCATION: (335)..(335)
<223> OTHER INFORMATION: Any naturally occurring amino acid
<220> FEATURE:
<221> NAME/KEY: MOD_RES
<222> LOCATION: (346)..(346)
<223> OTHER INFORMATION: Any naturally occurring amino acid
<220> FEATURE:
<221> NAME/KEY: MOD_RES
<222> LOCATION: (349)..(349)
<223> OTHER INFORMATION: Any naturally occurring amino acid
```

<400> SEQUENCE: 1

```
Met Asp Asp Glu Asn Glu Ser Ser Lys Ser Ala Gly Leu Lys Asn Ser
1               5                   10                  15

Asn Leu Glu Glu Xaa Glu Asp Lys Ile Ser Asn Lys Ile Glu Asn Ser
            20                  25                  30

Ser Val His Asn Asp Asp Asn Gly Asp Asp Arg Val Ile Asp Gly Ser
        35                  40                  45

Ser Gly Ala Glu Ser Leu Arg Glu Ser Lys Thr Glu Ala Leu Ile Ser
    50                  55                  60

Glu Thr Leu Ala His Pro Asn Ala Glu Ser Ser Val Gln Ile Glu Ile
65                  70                  75                  80

Asp Gly Gln Ser Glu Phe Asp Ser Glu Phe Ser Pro Ser Tyr Gln Leu
                85                  90                  95

Ser Glu Val Pro Val Glu Tyr Glu Leu Pro Ser Phe Gly Phe Ser Glu
            100                 105                 110

Lys Ile Lys Asp Arg Ile Ser Val Thr Lys Pro Gly Thr Leu Asn Ala
        115                 120                 125

Gln Ala Arg Thr Glu His Gln Arg Arg Val Pro Asp Ala Ala Ser Ser
    130                 135                 140

Leu Glu Leu Ser Ser Leu Ser Val Ala Gln Ser Ile Ser Ser Val Pro
145                 150                 155                 160

Ser Ala Thr Leu Ala Glu Arg Arg Ser Ala Ala Val Asn Cys Ser
                165                 170                 175

Thr Gly Glu Val Val Lys Gln Ser Ser Asp Ala Gln Val Leu Xaa Leu
            180                 185                 190

Val Pro Val Leu Lys Arg Pro Thr Arg Asp Gly Tyr Asn Trp Arg Lys
        195                 200                 205

Tyr Gly Gln Lys Gln Val Lys Ser Pro Gln Gly Ser Arg Ser Tyr Tyr
    210                 215                 220

Arg Cys Thr His Ser Glu Cys Cys Ala Lys Lys Ile Glu Cys Ser Asp
225                 230                 235                 240

His Thr Asn Arg Val Met Glu Ile Ile Tyr Arg Thr Gln His Asn His
                245                 250                 255

Asp Pro Pro Arg Val Asn Cys Xaa Arg Glu Ser Lys Ser Ala Val
            260                 265                 270

Leu Ser Ser Pro Thr Asn Gly Lys Ser Ile Ile Ala His Pro Xaa Arg
        275                 280                 285

Asn Ser Ile Glu Thr Val Val Ser Ser Leu Lys Glu Asn Leu Gln Glu
    290                 295                 300

Ser Leu Pro Ile Ala Glu Thr Ala Asn Gln Asp Ser Gly Gly Ser Asp
305                 310                 315                 320

Thr Asp Thr Glu Ile Thr Ile Arg Glu Glu His Arg Asp Glu Xaa Gly
                325                 330                 335

Gln Lys Lys Arg Ser Arg Lys Ser Asp Xaa Ser Cys Xaa Glu Ser Val
            340                 345                 350

Ser Lys Pro Gly Lys Lys Pro Lys Leu Val Val His Ala Ala Cys Asp
        355                 360                 365

Val Gly Ile Ser Ser Asp Gly Tyr Arg Trp Arg Lys Tyr Gly Gln Lys
    370                 375                 380

Met Val Lys Gly Asn Pro His Pro Arg Asn Tyr Tyr Arg Cys Thr Ser
385                 390                 395                 400

Ala Gly Cys Pro Val Arg Lys His Ile Glu Arg Val Val Asp Thr Thr
                405                 410                 415
```

```
Ser Ala Leu Thr Ile Thr Tyr Lys Gly Val His Asp His Asp Met Pro
            420                 425                 430

Val Pro Lys Lys Arg His Gly Pro Ser Ala Pro Leu Ile Ala Ala
            435                 440                 445

Thr Ala Pro Ala Ser Val Thr Asn Met His Ala Asn Lys Pro Glu Pro
    450                 455                 460

Leu Gln His Gln Lys Ser Thr Thr Gln Trp Ser Val Asp Lys Glu Gly
465                 470                 475                 480

Glu Leu Thr Gly Glu Lys Leu Asp Val Gly Gly Lys Ala Met Glu
                485                 490                 495

Ser Ala Arg Thr Leu Leu Ser Ile Gly Phe Glu Ile Lys Pro Cys
            500                 505                 510

<210> SEQ ID NO 2
<211> LENGTH: 467
<212> TYPE: PRT
<213> ORGANISM: Unknown
<220> FEATURE:
<223> OTHER INFORMATION: Description of Unknown:
      Brassicaceae sequence
<220> FEATURE:
<221> NAME/KEY: MOD_RES
<222> LOCATION: (5)..(5)
<223> OTHER INFORMATION: Any naturally occurring amino acid
<220> FEATURE:
<221> NAME/KEY: MOD_RES
<222> LOCATION: (77)..(77)
<223> OTHER INFORMATION: Any naturally occurring amino acid
<220> FEATURE:
<221> NAME/KEY: MOD_RES
<222> LOCATION: (92)..(92)
<223> OTHER INFORMATION: Any naturally occurring amino acid
<220> FEATURE:
<221> NAME/KEY: MOD_RES
<222> LOCATION: (104)..(104)
<223> OTHER INFORMATION: Any naturally occurring amino acid
<220> FEATURE:
<221> NAME/KEY: MOD_RES
<222> LOCATION: (109)..(109)
<223> OTHER INFORMATION: Any naturally occurring amino acid
<220> FEATURE:
<221> NAME/KEY: MOD_RES
<222> LOCATION: (112)..(112)
<223> OTHER INFORMATION: Any naturally occurring amino acid
<220> FEATURE:
<221> NAME/KEY: MOD_RES
<222> LOCATION: (124)..(124)
<223> OTHER INFORMATION: Any naturally occurring amino acid
<220> FEATURE:
<221> NAME/KEY: MOD_RES
<222> LOCATION: (132)..(133)
<223> OTHER INFORMATION: Any naturally occurring amino acid
<220> FEATURE:
<221> NAME/KEY: MOD_RES
<222> LOCATION: (246)..(246)
<223> OTHER INFORMATION: Any naturally occurring amino acid
<220> FEATURE:
<221> NAME/KEY: MOD_RES
<222> LOCATION: (265)..(265)
<223> OTHER INFORMATION: Any naturally occurring amino acid
<220> FEATURE:
<221> NAME/KEY: MOD_RES
<222> LOCATION: (318)..(318)
<223> OTHER INFORMATION: Any naturally occurring amino acid
<220> FEATURE:
<221> NAME/KEY: MOD_RES
<222> LOCATION: (320)..(320)
<223> OTHER INFORMATION: Any naturally occurring amino acid
<220> FEATURE:
<221> NAME/KEY: MOD_RES
<222> LOCATION: (375)..(375)
<223> OTHER INFORMATION: Any naturally occurring amino acid
```

<400> SEQUENCE: 2

```
Met Glu Asp Lys Xaa Ser Asp Glu Ala Asp Val Tyr Ala Ala Ala Glu
1               5                   10                  15

Thr Glu Lys Ser Glu Lys Val Glu Pro Glu Lys Glu Leu Cys Asp Gly
            20                  25                  30

Leu Ser Gln Leu Arg Asp Glu Glu Ser Leu Gly Ala Asp Met Glu
        35                  40                  45

Asp Leu His Asp Glu Pro Val Arg Glu Thr Leu Ala Lys Asp Gln Val
    50                  55                  60

Glu Gly Val Arg Glu Asn Ser Ser Val Glu Pro Asn Xaa Glu Asp Val
65                  70                  75                  80

Lys Glu Val Lys Glu Thr Asp Ser Gly Lys Glu Xaa Val Val Ser Ala
                85                  90                  95

Ile Val Pro Val Asp Glu Val Xaa Val Glu Asn Arg Xaa Val Glu Xaa
            100                 105                 110

Ser Pro Cys Leu Thr Ala Ser Ser Asp Pro Ser Xaa Val Glu Pro Ser
        115                 120                 125

Leu Ser Ser Xaa Xaa Ser Ala Ala Gln Gly Leu Ser Leu Val Ser Val
130                 135                 140

Pro Thr Lys Gln Glu Gln Arg Ser Asp Ser Arg Val Val Asn Asn Leu
145                 150                 155                 160

Ser Val Ser Pro Val Leu Arg Thr Pro Ala Arg Asp Gly Tyr Asn Trp
                165                 170                 175

Arg Lys Tyr Gly Gln Lys Gln Val Lys Ser Pro Lys Gly Ser Arg Ser
            180                 185                 190

Tyr Tyr Arg Cys Thr Tyr Ser Glu Cys Cys Ala Lys Lys Ile Glu Cys
        195                 200                 205

Ser Asn Asp Ser Gly Asn Val Ile Glu Ile Val Asn Lys Gly Leu His
    210                 215                 220

Ser His Glu Pro Pro Arg Lys Asn Ser Phe Ser Pro Arg Glu Ile Arg
225                 230                 235                 240

Ala Ala Ser Ala Ile Xaa Pro Val Ser Glu Asp Asn Thr Val Val Glu
                245                 250                 255

Glu Ile Val Pro Ser Gly Ser Asp Xaa Ser Ala Ser Thr Lys Glu Asn
            260                 265                 270

Ile Cys Gln Ser Leu Thr Ile Val Glu Arg Lys Arg His Cys Glu Asn
        275                 280                 285

Glu Ala Val Glu Glu Pro Glu Pro Lys Arg Arg Leu Lys Lys Asp Asn
    290                 295                 300

Ser Gln Ser Ser Asp Ser Val Ser Lys Pro Gly Lys Lys Xaa Lys Xaa
305                 310                 315                 320

Val Val His Ala Ala Gly Asp Val Gly Ile Ser Gly Asp Gly Tyr Arg
                325                 330                 335

Trp Arg Lys Tyr Gly Gln Lys Met Val Lys Gly Asn Pro Asn Pro Arg
            340                 345                 350

Asn Tyr Tyr Arg Cys Thr Ser Ala Gly Cys Pro Val Arg Lys His Ile
        355                 360                 365

Glu Thr Ala Val Glu Asn Xaa Thr Ala Val Ile Ile Thr Tyr Lys Gly
    370                 375                 380

Val His Asn His Asp Met Pro Val Pro Lys Lys Arg His Gly Pro Pro
385                 390                 395                 400

Ser Ser Met Leu Val Ala Ala Ala Pro Thr Ser Met Arg Thr Arg
```

Leu Asp Asp Gln Val Asn Ile Pro Thr Ser Ser Gln Cys Ser Val Gly
            420                 425                 430

Arg Glu Ser Glu Lys Gln Ser Ser Glu Ala Val Asp Val Gly Gly Glu
        435                 440                 445

Lys Val Met Glu Ser Ala Arg Thr Leu Leu Ser Ile Gly Phe Glu Ile
    450                 455                 460

Lys Gln Cys
465

<210> SEQ ID NO 3
<211> LENGTH: 487
<212> TYPE: PRT
<213> ORGANISM: Unknown
<220> FEATURE:
<223> OTHER INFORMATION: Description of Unknown:
      Cucurbitaceae sequence
<220> FEATURE:
<221> NAME/KEY: MOD_RES
<222> LOCATION: (19)..(20)
<223> OTHER INFORMATION: Any naturally occurring amino acid
<220> FEATURE:
<221> NAME/KEY: MOD_RES
<222> LOCATION: (23)..(23)
<223> OTHER INFORMATION: Any naturally occurring amino acid
<220> FEATURE:
<221> NAME/KEY: MOD_RES
<222> LOCATION: (35)..(35)
<223> OTHER INFORMATION: Any naturally occurring amino acid
<220> FEATURE:
<221> NAME/KEY: MOD_RES
<222> LOCATION: (38)..(38)
<223> OTHER INFORMATION: Any naturally occurring amino acid
<220> FEATURE:
<221> NAME/KEY: MOD_RES
<222> LOCATION: (40)..(40)
<223> OTHER INFORMATION: Any naturally occurring amino acid
<220> FEATURE:
<221> NAME/KEY: MOD_RES
<222> LOCATION: (52)..(52)
<223> OTHER INFORMATION: Any naturally occurring amino acid
<220> FEATURE:
<221> NAME/KEY: MOD_RES
<222> LOCATION: (66)..(66)
<223> OTHER INFORMATION: Any naturally occurring amino acid
<220> FEATURE:
<221> NAME/KEY: MOD_RES
<222> LOCATION: (69)..(69)
<223> OTHER INFORMATION: Any naturally occurring amino acid
<220> FEATURE:
<221> NAME/KEY: MOD_RES
<222> LOCATION: (73)..(73)
<223> OTHER INFORMATION: Any naturally occurring amino acid
<220> FEATURE:
<221> NAME/KEY: MOD_RES
<222> LOCATION: (104)..(104)
<223> OTHER INFORMATION: Any naturally occurring amino acid
<220> FEATURE:
<221> NAME/KEY: MOD_RES
<222> LOCATION: (143)..(143)
<223> OTHER INFORMATION: Any naturally occurring amino acid
<220> FEATURE:
<221> NAME/KEY: MOD_RES
<222> LOCATION: (147)..(147)
<223> OTHER INFORMATION: Any naturally occurring amino acid
<220> FEATURE:
<221> NAME/KEY: MOD_RES
<222> LOCATION: (237)..(237)
<223> OTHER INFORMATION: Any naturally occurring amino acid
<220> FEATURE:
<221> NAME/KEY: MOD_RES
<222> LOCATION: (300)..(300)
<223> OTHER INFORMATION: Any naturally occurring amino acid
<220> FEATURE:

```
<221> NAME/KEY: MOD_RES
<222> LOCATION: (308)..(308)
<223> OTHER INFORMATION: Any naturally occurring amino acid
<220> FEATURE:
<221> NAME/KEY: MOD_RES
<222> LOCATION: (310)..(310)
<223> OTHER INFORMATION: Any naturally occurring amino acid
<220> FEATURE:
<221> NAME/KEY: MOD_RES
<222> LOCATION: (433)..(433)
<223> OTHER INFORMATION: Any naturally occurring amino acid

<400> SEQUENCE: 3

Met Glu Asp Ser Asp Glu Ser Glu Val Glu Leu Glu Gly Glu Gly
1               5                   10                  15

Gly Gly Xaa Xaa Ser Glu Xaa Lys Pro Thr Glu Leu Arg Thr Gly Ser
            20                  25                  30

Ser Val Xaa Glu Ala Xaa Val Xaa Gly Ser Leu Ser Thr Leu Thr
            35                  40                  45

Val Ala Ser Xaa Asn Gln Ser Ser Glu Asn Gly Arg Ser Asp Gly Leu
50                  55                  60

Pro Xaa Asn Ser Xaa Ala Gln Ser Xaa Glu Gly Ala Glu Leu Lys Gln
65                  70                  75                  80

Ala Pro Ser Ser His Ser Glu Pro Leu Ala Val Glu Ala Thr Gln Thr
                85                  90                  95

Asp Lys Val Gln Glu Gln Asn Xaa Leu Gln Leu Thr Val Phe Lys Gly
            100                 105                 110

Pro Asp Ser Glu Gln Ser Pro Thr Ser Val Thr Gln Ser Ile Ser Ser
            115                 120                 125

Ser Ala Ser Pro Asn Leu Ser Glu His Lys Leu Ser Pro Lys Xaa Val
130                 135                 140

Gln Lys Xaa Cys Lys Pro Glu Pro Ser Gln Lys Asn Phe Phe Asn His
145                 150                 155                 160

Lys Thr Pro Ser Ser Val Pro Asn Ala Arg Thr Pro Ala Ser Asp Gly
                165                 170                 175

Tyr Asn Trp Arg Lys Tyr Gly Gln Lys Gln Val Lys Ser Pro Lys Gly
            180                 185                 190

Ser Arg Ser Tyr Tyr Lys Cys Thr Tyr Ser Glu Cys Phe Ala Lys Lys
            195                 200                 205

Ile Glu Cys Cys Asp Asp Ser Gly Gln Thr Thr Glu Ile Val Tyr Lys
210                 215                 220

Ser Gln His Ser His Asp Pro Pro Arg Lys Ile Ser Xaa Pro Lys Glu
225                 230                 235                 240

Ser Lys Leu Val Pro Tyr Val Glu Pro Val Val Lys Lys Ile Ile Ala
                245                 250                 255

Glu His Ser Arg Arg Val Ile Asn Asp Ser Asp Pro Pro Thr Ser Ser
            260                 265                 270

Lys Glu Pro Leu Arg Glu Thr Ala Ile Val Val Phe Glu Arg Lys Arg
            275                 280                 285

Gln Tyr Ser Asn Asp Ser Asn Gly Asn Asp Glu Xaa Lys Ile Lys Asp
290                 295                 300

Glu Asn Asp Xaa Glu Xaa Glu Thr Lys Gln Lys Val Lys Lys Ser Ser
305                 310                 315                 320

Ala Gly Asn Ser Gly Thr Pro Leu Lys Pro Gly Lys Lys Pro Lys Phe
                325                 330                 335

Val Val His Ala Ala Gly Asp Val Gly Ile Ser Gly Asp Gly Tyr Arg
            340                 345                 350
```

-continued

```
Trp Arg Lys Tyr Gly Gln Lys Met Val Lys Gly Asn Pro His Pro Arg
        355                 360                 365

Asn Tyr Tyr Arg Cys Thr Ser Ala Gly Cys Pro Val Arg Lys His Ile
    370                 375                 380

Glu Ser Ala Val Glu Asn Pro Asn Ala Val Ile Ile Thr Tyr Lys Gly
385                 390                 395                 400

Val His Asp His Asp Thr Pro Val Pro Lys Lys Arg His Gly Pro Pro
                405                 410                 415

Ser Ala Leu Leu Val Ala Ala Ala Pro Ala Ser Met Ser Ser Asn
            420                 425                 430

Xaa Gln Pro Lys Lys Thr Asp Val Val Glu Ser Gln Ile Ser Ser Thr
            435                 440                 445

Gln Trp Ser Val Asp Ala Glu Gly Glu Leu Thr Gly Glu Ala Leu Glu
        450                 455                 460

Leu Gly Gly Glu Lys Ala Met Glu Ser Ala Arg Thr Leu Leu Ser Ile
465                 470                 475                 480

Gly Phe Glu Ile Lys Pro Cys
                485

<210> SEQ ID NO 4
<211> LENGTH: 503
<212> TYPE: PRT
<213> ORGANISM: Unknown
<220> FEATURE:
<223> OTHER INFORMATION: Description of Unknown:
      Fabaceae sequence
<220> FEATURE:
<221> NAME/KEY: MOD_RES
<222> LOCATION: (14)..(17)
<223> OTHER INFORMATION: Any naturally occurring amino acid
<220> FEATURE:
<221> NAME/KEY: MOD_RES
<222> LOCATION: (21)..(21)
<223> OTHER INFORMATION: Any naturally occurring amino acid
<220> FEATURE:
<221> NAME/KEY: MOD_RES
<222> LOCATION: (29)..(29)
<223> OTHER INFORMATION: Any naturally occurring amino acid
<220> FEATURE:
<221> NAME/KEY: MOD_RES
<222> LOCATION: (33)..(33)
<223> OTHER INFORMATION: Any naturally occurring amino acid
<220> FEATURE:
<221> NAME/KEY: MOD_RES
<222> LOCATION: (45)..(45)
<223> OTHER INFORMATION: Any naturally occurring amino acid
<220> FEATURE:
<221> NAME/KEY: MOD_RES
<222> LOCATION: (90)..(90)
<223> OTHER INFORMATION: Any naturally occurring amino acid
<220> FEATURE:
<221> NAME/KEY: MOD_RES
<222> LOCATION: (108)..(108)
<223> OTHER INFORMATION: Any naturally occurring amino acid
<220> FEATURE:
<221> NAME/KEY: MOD_RES
<222> LOCATION: (165)..(165)
<223> OTHER INFORMATION: Any naturally occurring amino acid
<220> FEATURE:
<221> NAME/KEY: MOD_RES
<222> LOCATION: (275)..(275)
<223> OTHER INFORMATION: Any naturally occurring amino acid
<220> FEATURE:
<221> NAME/KEY: MOD_RES
<222> LOCATION: (284)..(284)
<223> OTHER INFORMATION: Any naturally occurring amino acid
<220> FEATURE:
<221> NAME/KEY: MOD_RES
<222> LOCATION: (301)..(301)
```

-continued

<223> OTHER INFORMATION: Any naturally occurring amino acid
<220> FEATURE:
<221> NAME/KEY: MOD_RES
<222> LOCATION: (306)..(306)
<223> OTHER INFORMATION: Any naturally occurring amino acid

<400> SEQUENCE: 4

Met Ala Glu Arg Gly Ser Pro Gln Leu Leu Pro Glu Pro Xaa Xaa Xaa
1               5                   10                  15

Xaa Asn Asp Ser Xaa Gln Lys Pro Lys Ala Ala Glu Xaa Thr Glu Arg
            20                  25                  30

Xaa Thr Glu Ser Pro Ser Ala Ala Glu Ser Gln Arg Xaa Glu Leu Arg
        35                  40                  45

Ser Ser Asp Glu Pro Arg Thr Glu Ser Asn Leu Glu Thr Leu Gly Ala
50                  55                  60

Ala Ser Ser Val Thr Leu Ala Val Gln His His Arg Ser Asp Asp Leu
65                  70                  75                  80

Gln Gly Ser Ser Ala Ala Pro Asn Ser Xaa Gly Lys Ala Glu Ser Lys
                85                  90                  95

Glu Thr Val Gly Pro Pro Glu Lys Glu Ile Ile Xaa Arg Gly Ala Ala
            100                 105                 110

Gln Pro Leu Pro Thr Gln Thr Glu Asn Arg Leu Gln Val Ser Val Cys
        115                 120                 125

Ser Thr Pro Leu Ser Glu Leu Ser Pro Thr Ser Val Thr Gln Ser Leu
130                 135                 140

Ser Ser Val Ser Ser Pro Thr Val Pro Lys Gln Lys Met Ser Thr Pro
145                 150                 155                 160

Lys Val Asn Asn Xaa His Val Pro Glu Val Asp Lys Lys Asn Pro Ser
                165                 170                 175

Gly Gly Lys Thr Leu Ser Ala Val Ser Val Ala Arg Thr Ser Ala Ser
            180                 185                 190

Asp Gly Tyr Asn Trp Arg Lys Tyr Gly Gln Lys Gln Val Lys Ser Pro
        195                 200                 205

Thr Gly Ser Arg Ser Tyr Tyr Arg Cys Thr His Ser Asp Cys Cys Ala
210                 215                 220

Lys Lys Ile Glu Cys Cys Asp His Ser Gly His Val Ile Glu Ile Val
225                 230                 235                 240

Tyr Lys Ser Glu His Ser His Asp Pro Pro Arg Lys Thr Asn Ser Ile
                245                 250                 255

Arg Glu Asn Lys Phe Leu Ser Ser Ser Glu Pro Ile Val Glu Asn Ser
            260                 265                 270

Val Pro Xaa Gln Pro Val Arg Val Leu Lys Asp Xaa Asp Pro Ser Ile
        275                 280                 285

Ser Ser Lys Glu Ser Leu Gln Glu Ala Pro Cys Ser Xaa Asp Lys Lys
290                 295                 300

Arg Xaa Asn Ser Ser Asn Ile Ser Gly Asn Gly Lys Val Ile Leu Lys
305                 310                 315                 320

Glu Glu His Val Asn Glu Pro Glu Pro Lys Lys Arg Met Lys Lys Gly
                325                 330                 335

Asp Leu Thr Asp Met Asp Ser Pro Val Lys Pro Gly Lys Lys Pro Lys
            340                 345                 350

Phe Val Val His Ala Ala Gly Asp Val Gly Ile Ser Gly Asp Gly Tyr
        355                 360                 365

Arg Trp Arg Lys Tyr Gly Gln Lys Met Val Lys Gly Asn Pro His Pro
370                 375                 380

```
Arg Asn Tyr Tyr Arg Cys Thr Ser Ala Gly Cys Pro Val Arg Lys His
385                 390                 395                 400

Ile Glu Thr Ala Val Asp Asn Ser Asp Ala Val Ile Ile Thr Tyr Lys
            405                 410                 415

Gly Val His Asp His Asp Met Pro Val Pro Lys Lys Arg His Gly Pro
            420                 425                 430

Pro Ser Ala Pro Leu Val Ala Ala Ala Pro Ala Ser Met Asn Ser
        435                 440                 445

Leu Gln Val Lys Lys Pro Asp Ser Pro Gln Asn Lys Lys Ile Ser Thr
    450                 455                 460

Gln Trp Ser Val Asp Thr Glu Gly Glu Leu Thr Gly Glu Ala Leu Glu
465                 470                 475                 480

Leu Gly Gly Glu Lys Ala Met Glu Ser Ala Arg Thr Leu Leu Ser Ile
                485                 490                 495

Gly Phe Glu Ile Lys Pro Cys
                500

<210> SEQ ID NO 5
<211> LENGTH: 506
<212> TYPE: PRT
<213> ORGANISM: Unknown
<220> FEATURE:
<223> OTHER INFORMATION: Description of Unknown:
      Rosaceae sequence
<220> FEATURE:
<221> NAME/KEY: MOD_RES
<222> LOCATION: (4)..(4)
<223> OTHER INFORMATION: Any naturally occurring amino acid
<220> FEATURE:
<221> NAME/KEY: MOD_RES
<222> LOCATION: (8)..(8)
<223> OTHER INFORMATION: Any naturally occurring amino acid
<220> FEATURE:
<221> NAME/KEY: MOD_RES
<222> LOCATION: (12)..(13)
<223> OTHER INFORMATION: Any naturally occurring amino acid
<220> FEATURE:
<221> NAME/KEY: MOD_RES
<222> LOCATION: (17)..(17)
<223> OTHER INFORMATION: Any naturally occurring amino acid
<220> FEATURE:
<221> NAME/KEY: MOD_RES
<222> LOCATION: (19)..(21)
<223> OTHER INFORMATION: Any naturally occurring amino acid
<220> FEATURE:
<221> NAME/KEY: MOD_RES
<222> LOCATION: (26)..(27)
<223> OTHER INFORMATION: Any naturally occurring amino acid
<220> FEATURE:
<221> NAME/KEY: MOD_RES
<222> LOCATION: (33)..(33)
<223> OTHER INFORMATION: Any naturally occurring amino acid
<220> FEATURE:
<221> NAME/KEY: MOD_RES
<222> LOCATION: (35)..(35)
<223> OTHER INFORMATION: Any naturally occurring amino acid
<220> FEATURE:
<221> NAME/KEY: MOD_RES
<222> LOCATION: (37)..(39)
<223> OTHER INFORMATION: Any naturally occurring amino acid
<220> FEATURE:
<221> NAME/KEY: MOD_RES
<222> LOCATION: (44)..(44)
<223> OTHER INFORMATION: Any naturally occurring amino acid
<220> FEATURE:
<221> NAME/KEY: MOD_RES
<222> LOCATION: (46)..(46)
<223> OTHER INFORMATION: Any naturally occurring amino acid
<220> FEATURE:
<221> NAME/KEY: MOD_RES
```

```
<222> LOCATION: (50)..(51)
<223> OTHER INFORMATION: Any naturally occurring amino acid
<220> FEATURE:
<221> NAME/KEY: MOD_RES
<222> LOCATION: (53)..(54)
<223> OTHER INFORMATION: Any naturally occurring amino acid
<220> FEATURE:
<221> NAME/KEY: MOD_RES
<222> LOCATION: (56)..(56)
<223> OTHER INFORMATION: Any naturally occurring amino acid
<220> FEATURE:
<221> NAME/KEY: MOD_RES
<222> LOCATION: (70)..(70)
<223> OTHER INFORMATION: Any naturally occurring amino acid
<220> FEATURE:
<221> NAME/KEY: MOD_RES
<222> LOCATION: (78)..(78)
<223> OTHER INFORMATION: Any naturally occurring amino acid
<220> FEATURE:
<221> NAME/KEY: MOD_RES
<222> LOCATION: (81)..(81)
<223> OTHER INFORMATION: Any naturally occurring amino acid
<220> FEATURE:
<221> NAME/KEY: MOD_RES
<222> LOCATION: (84)..(84)
<223> OTHER INFORMATION: Any naturally occurring amino acid
<220> FEATURE:
<221> NAME/KEY: MOD_RES
<222> LOCATION: (86)..(86)
<223> OTHER INFORMATION: Any naturally occurring amino acid
<220> FEATURE:
<221> NAME/KEY: MOD_RES
<222> LOCATION: (94)..(94)
<223> OTHER INFORMATION: Any naturally occurring amino acid
<220> FEATURE:
<221> NAME/KEY: MOD_RES
<222> LOCATION: (101)..(101)
<223> OTHER INFORMATION: Any naturally occurring amino acid
<220> FEATURE:
<221> NAME/KEY: MOD_RES
<222> LOCATION: (112)..(112)
<223> OTHER INFORMATION: Any naturally occurring amino acid
<220> FEATURE:
<221> NAME/KEY: MOD_RES
<222> LOCATION: (117)..(117)
<223> OTHER INFORMATION: Any naturally occurring amino acid
<220> FEATURE:
<221> NAME/KEY: MOD_RES
<222> LOCATION: (122)..(123)
<223> OTHER INFORMATION: Any naturally occurring amino acid
<220> FEATURE:
<221> NAME/KEY: MOD_RES
<222> LOCATION: (155)..(155)
<223> OTHER INFORMATION: Any naturally occurring amino acid
<220> FEATURE:
<221> NAME/KEY: MOD_RES
<222> LOCATION: (159)..(159)
<223> OTHER INFORMATION: Any naturally occurring amino acid
<220> FEATURE:
<221> NAME/KEY: MOD_RES
<222> LOCATION: (161)..(161)
<223> OTHER INFORMATION: Any naturally occurring amino acid
<220> FEATURE:
<221> NAME/KEY: MOD_RES
<222> LOCATION: (275)..(275)
<223> OTHER INFORMATION: Any naturally occurring amino acid
<220> FEATURE:
<221> NAME/KEY: MOD_RES
<222> LOCATION: (336)..(336)
<223> OTHER INFORMATION: Any naturally occurring amino acid
<220> FEATURE:
<221> NAME/KEY: MOD_RES
<222> LOCATION: (345)..(345)
<223> OTHER INFORMATION: Any naturally occurring amino acid
<220> FEATURE:
<221> NAME/KEY: MOD_RES
<222> LOCATION: (408)..(408)
<223> OTHER INFORMATION: Any naturally occurring amino acid
<220> FEATURE:
```

<221> NAME/KEY: MOD_RES
<222> LOCATION: (461)..(461)
<223> OTHER INFORMATION: Any naturally occurring amino acid

<400> SEQUENCE: 5

```
Met Ala Glu Xaa His Glu Ser Xaa Asp Ala Leu Xaa Xaa Lys Leu
1               5                   10                  15

Xaa Pro Xaa Xaa Xaa Glu Gln Glu Glu Xaa Xaa Glu Gly Asp Glu
                20                  25                  30

Xaa Asp Xaa Glu Xaa Xaa Xaa Arg Leu Gly Glu Xaa Gln Xaa Gly Glu
            35                  40                  45

Leu Xaa Xaa Ser Xaa Xaa Glu Xaa Arg Glu Thr Gln Leu Glu Thr Leu
    50                  55                  60

Ala Val Pro Ser Thr Xaa Glu Leu Ser Glu Asn Asp Gln Xaa Ala Gly
65                  70                  75                  80

Xaa Gln Val Xaa Ser Xaa Ser Gln Ser Ile Asp Gly Ala Xaa Leu Gln
                85                  90                  95

Glu Gln Leu Gly Xaa Ser His Gln Glu Ile Leu Ala Ser Val Thr Xaa
                100                 105                 110

Gln Asp Ser Gln Xaa Gln Thr Gln Ser Xaa Xaa Gln Leu Gln Leu Thr
            115                 120                 125

Val Tyr Pro Thr Pro Leu Ser Glu Leu Ser Pro Thr Ser Val Thr Gln
            130                 135                 140

Ser Ile Ser Ser Ala Pro Ser Pro Ile Leu Xaa Glu Gln Arg Xaa Pro
145                 150                 155                 160

Xaa Glu Lys Val Asn Thr Leu Cys Thr Pro Glu Val Asp Lys Gln Asn
                165                 170                 175

Ser Ser Asp His Lys Phe Ile Ser Ser Val Pro Leu Val Lys Thr Ser
            180                 185                 190

Ala Ser Asp Gly Tyr Asn Trp Arg Lys Tyr Gly Gln Lys Gln Val Lys
        195                 200                 205

Ser Pro Gln Gly Ser Arg Ser Tyr Tyr Arg Cys Thr Tyr Ser Glu Cys
    210                 215                 220

Tyr Ala Lys Lys Ile Glu Cys Cys Asp His Ser Gly His Val Thr Glu
225                 230                 235                 240

Ile Val Tyr Lys Ser Gln His Thr His Asp Pro Pro Arg Lys Ser Asn
                245                 250                 255

Cys Thr Lys Glu Ser Lys Leu Ala Leu Ser Ala Glu Cys Val Arg Asn
            260                 265                 270

Ser Val Xaa Glu His Pro Cys Arg Thr Val Asn Asp Ser Glu Val Ser
        275                 280                 285

Thr Ser Ser Lys Glu Pro Ile Gln Glu Thr Pro Ser Val Pro Glu Arg
290                 295                 300

Lys Arg Gln Ser Pro Ser Asp Ser Asp Gly Asn Gly Asp Val Lys Ile
305                 310                 315                 320

Lys Glu Glu His Gly Asp Gly Asp Glu Pro Pro Lys Arg Arg Xaa
                325                 330                 335

Lys Lys Ser Asn Ser Glu Tyr Ser Xaa Ser Leu Leu Lys Pro Gly Lys
            340                 345                 350

Lys Pro Lys Phe Val Val His Ala Ala Gly Asp Val Gly Ile Ser Gly
        355                 360                 365

Asp Gly Tyr Arg Trp Arg Lys Tyr Gly Gln Lys Met Val Lys Gly Asn
370                 375                 380

Pro His Pro Arg Asn Tyr Tyr Arg Cys Thr Ser Ala Gly Cys Pro Val
```

-continued

```
            385                 390                 395                 400
Arg Lys His Ile Glu Thr Ala Xaa Asp Asn Thr Ser Ala Val Ile Ile
                    405                 410                 415

Thr Tyr Lys Gly Ile His Asp His Asp Met Pro Val Pro Lys Lys Arg
                420                 425                 430

His Gly Pro Pro Ser Ala Pro Leu Val Ala Ala Ala Pro Ala Ser
            435                 440                 445

Met Asn Asn Leu His Ile Lys Lys Thr Asp Thr His Xaa Asn Gln Ile
    450                 455                 460

Ser Ser Thr Gln Trp Ser Val Asp Thr Gly Gly Glu Leu Thr Gly Glu
465                 470                 475                 480

Ala Leu Asp Leu Gly Gly Glu Lys Ala Met Glu Ser Ala Arg Thr Leu
                485                 490                 495

Leu Ser Ile Gly Phe Glu Ile Lys Pro Cys
            500                 505

<210> SEQ ID NO 6
<211> LENGTH: 558
<212> TYPE: PRT
<213> ORGANISM: Unknown
<220> FEATURE:
<223> OTHER INFORMATION: Description of Unknown:
      Poaceae sequence
<220> FEATURE:
<221> NAME/KEY: MOD_RES
<222> LOCATION: (9)..(9)
<223> OTHER INFORMATION: Any naturally occurring amino acid
<220> FEATURE:
<221> NAME/KEY: MOD_RES
<222> LOCATION: (12)..(12)
<223> OTHER INFORMATION: Any naturally occurring amino acid
<220> FEATURE:
<221> NAME/KEY: MOD_RES
<222> LOCATION: (36)..(36)
<223> OTHER INFORMATION: Any naturally occurring amino acid
<220> FEATURE:
<221> NAME/KEY: MOD_RES
<222> LOCATION: (38)..(38)
<223> OTHER INFORMATION: Any naturally occurring amino acid
<220> FEATURE:
<221> NAME/KEY: MOD_RES
<222> LOCATION: (43)..(43)
<223> OTHER INFORMATION: Any naturally occurring amino acid
<220> FEATURE:
<221> NAME/KEY: MOD_RES
<222> LOCATION: (45)..(46)
<223> OTHER INFORMATION: Any naturally occurring amino acid
<220> FEATURE:
<221> NAME/KEY: MOD_RES
<222> LOCATION: (54)..(55)
<223> OTHER INFORMATION: Any naturally occurring amino acid
<220> FEATURE:
<221> NAME/KEY: MOD_RES
<222> LOCATION: (62)..(62)
<223> OTHER INFORMATION: Any naturally occurring amino acid
<220> FEATURE:
<221> NAME/KEY: MOD_RES
<222> LOCATION: (66)..(66)
<223> OTHER INFORMATION: Any naturally occurring amino acid
<220> FEATURE:
<221> NAME/KEY: MOD_RES
<222> LOCATION: (69)..(69)
<223> OTHER INFORMATION: Any naturally occurring amino acid
<220> FEATURE:
<221> NAME/KEY: MOD_RES
<222> LOCATION: (74)..(74)
<223> OTHER INFORMATION: Any naturally occurring amino acid
<220> FEATURE:
<221> NAME/KEY: MOD_RES
<222> LOCATION: (82)..(82)
<223> OTHER INFORMATION: Any naturally occurring amino acid
```

```
<220> FEATURE:
<221> NAME/KEY: MOD_RES
<222> LOCATION: (90)..(90)
<223> OTHER INFORMATION: Any naturally occurring amino acid
<220> FEATURE:
<221> NAME/KEY: MOD_RES
<222> LOCATION: (97)..(97)
<223> OTHER INFORMATION: Any naturally occurring amino acid
<220> FEATURE:
<221> NAME/KEY: MOD_RES
<222> LOCATION: (99)..(99)
<223> OTHER INFORMATION: Any naturally occurring amino acid
<220> FEATURE:
<221> NAME/KEY: MOD_RES
<222> LOCATION: (103)..(105)
<223> OTHER INFORMATION: Any naturally occurring amino acid
<220> FEATURE:
<221> NAME/KEY: MOD_RES
<222> LOCATION: (107)..(107)
<223> OTHER INFORMATION: Any naturally occurring amino acid
<220> FEATURE:
<221> NAME/KEY: MOD_RES
<222> LOCATION: (113)..(113)
<223> OTHER INFORMATION: Any naturally occurring amino acid
<220> FEATURE:
<221> NAME/KEY: MOD_RES
<222> LOCATION: (118)..(118)
<223> OTHER INFORMATION: Any naturally occurring amino acid
<220> FEATURE:
<221> NAME/KEY: MOD_RES
<222> LOCATION: (126)..(126)
<223> OTHER INFORMATION: Any naturally occurring amino acid
<220> FEATURE:
<221> NAME/KEY: MOD_RES
<222> LOCATION: (193)..(193)
<223> OTHER INFORMATION: Any naturally occurring amino acid
<220> FEATURE:
<221> NAME/KEY: MOD_RES
<222> LOCATION: (196)..(196)
<223> OTHER INFORMATION: Any naturally occurring amino acid
<220> FEATURE:
<221> NAME/KEY: MOD_RES
<222> LOCATION: (213)..(213)
<223> OTHER INFORMATION: Any naturally occurring amino acid
<220> FEATURE:
<221> NAME/KEY: MOD_RES
<222> LOCATION: (218)..(218)
<223> OTHER INFORMATION: Any naturally occurring amino acid
<220> FEATURE:
<221> NAME/KEY: MOD_RES
<222> LOCATION: (224)..(224)
<223> OTHER INFORMATION: Any naturally occurring amino acid
<220> FEATURE:
<221> NAME/KEY: MOD_RES
<222> LOCATION: (226)..(226)
<223> OTHER INFORMATION: Any naturally occurring amino acid
<220> FEATURE:
<221> NAME/KEY: MOD_RES
<222> LOCATION: (299)..(299)
<223> OTHER INFORMATION: Any naturally occurring amino acid
<220> FEATURE:
<221> NAME/KEY: MOD_RES
<222> LOCATION: (304)..(304)
<223> OTHER INFORMATION: Any naturally occurring amino acid
<220> FEATURE:
<221> NAME/KEY: MOD_RES
<222> LOCATION: (313)..(313)
<223> OTHER INFORMATION: Any naturally occurring amino acid
<220> FEATURE:
<221> NAME/KEY: MOD_RES
<222> LOCATION: (328)..(328)
<223> OTHER INFORMATION: Any naturally occurring amino acid
<220> FEATURE:
<221> NAME/KEY: MOD_RES
<222> LOCATION: (337)..(337)
<223> OTHER INFORMATION: Any naturally occurring amino acid
<220> FEATURE:
<221> NAME/KEY: MOD_RES
<222> LOCATION: (342)..(342)
```

```
<223> OTHER INFORMATION: Any naturally occurring amino acid
<220> FEATURE:
<221> NAME/KEY: MOD_RES
<222> LOCATION: (447)..(447)
<223> OTHER INFORMATION: Any naturally occurring amino acid
<220> FEATURE:
<221> NAME/KEY: MOD_RES
<222> LOCATION: (479)..(479)
<223> OTHER INFORMATION: Any naturally occurring amino acid
<220> FEATURE:
<221> NAME/KEY: MOD_RES
<222> LOCATION: (485)..(485)
<223> OTHER INFORMATION: Any naturally occurring amino acid
<220> FEATURE:
<221> NAME/KEY: MOD_RES
<222> LOCATION: (491)..(491)
<223> OTHER INFORMATION: Any naturally occurring amino acid
<220> FEATURE:
<221> NAME/KEY: MOD_RES
<222> LOCATION: (508)..(509)
<223> OTHER INFORMATION: Any naturally occurring amino acid

<400> SEQUENCE: 6

Met Ala Asp Gly Asp Pro Ala Xaa Pro Glu Xaa Lys Arg Pro Ala
1               5                   10                  15

Pro Glu Ala Ala Glu Ala Glu Ala His Pro Pro Glu Pro Pro Gly
            20                  25                  30

Ala Lys Pro Xaa Glu Xaa Glu Glu Gly Glu Xaa Gly Xaa Xaa Lys Glu
        35                  40                  45

Glu Lys Val Glu Ala Xaa Asp Met Glu Gly Lys Gly Xaa Glu Lys
        50                  55                  60

Glu Xaa Gly Asp Xaa Ala Lys Glu Lys Xaa Glu Glu Asp Lys Gly
65                  70                  75                  80

Lys Xaa Lys Glu Gly Lys Gly Lys Glu Xaa Glu Thr Lys Glu Lys Val
            85                  90                  95

Xaa Val Xaa Ala Lys Lys Xaa Xaa Ala Xaa Glu Lys Glu Lys Gly
        100                 105                 110

Xaa Glu Lys Glu Val Xaa Ala Thr Arg Arg Pro Ala Gly Xaa Ser Ala
            115                 120                 125

Glu Thr Pro Ile Leu Ala Val Pro Met Val Ala Val Pro Cys Phe Ile
130                 135                 140

Ala Pro Pro Gly Phe Ala Gly Gln Phe Ala Met Ser His Gln Ala Ala
145                 150                 155                 160

Leu Ala Ser Val Thr Ala Gln Ala Gln Met Gln Leu Gln Ser Pro Thr
            165                 170                 175

Thr Ser Ala Tyr Ser Glu Gly Leu Pro Ser Pro Phe Pro Ile Thr Pro
        180                 185                 190

Xaa Ala Val Xaa Pro Leu Gln Gln Ser Pro Ser Val Thr Glu Gly Asn
            195                 200                 205

Val Cys Arg Pro Xaa Ala Glu Lys Ser Xaa Ser Ser Gln Ser Lys Xaa
210                 215                 220

Pro Xaa His His Val Ser Val Asn Met Val Gly Asp Gly Phe Asn Trp
225                 230                 235                 240

Arg Lys Tyr Gly Gln Lys Gln Val Lys Ser Ser Glu Asn Ser Arg Ser
            245                 250                 255

Tyr Tyr Arg Cys Thr Asn Ser Gly Cys Leu Ala Lys Lys Lys Val Glu
        260                 265                 270

His Cys Pro Asp Gly Arg Val Val Glu Ile Ile Tyr Arg Gly Thr His
    275                 280                 285

Asn His Glu Pro Pro Gln Lys Thr Arg Phe Xaa Lys Glu Arg Val Xaa
```

-continued

```
            290                 295                 300

His Ile Thr Val Ser Ser Gly Asp Xaa Glu Thr Leu Arg Leu Val Asn
305                 310                 315                 320

Thr Glu Ile Ile Glu Ser Ser Xaa Pro Pro Gly Cys Lys Leu Glu Pro
                325                 330                 335

Xaa Ala Val Ser Glu Xaa Ser Glu Gln Gln Leu Phe Cys Ser Ser Asp
            340                 345                 350

Cys Glu Gly Asp Ala Gly Asn Lys Ser Glu Asp Glu His Pro Ser Ala
        355                 360                 365

Glu Pro Gln Pro Lys Arg Arg Ile Ile Glu Thr Thr Thr Pro Asn Leu
    370                 375                 380

Thr Pro Val Leu Arg Thr Val Arg Glu Gln Lys Ile Ile Val Gln Ala
385                 390                 395                 400

Gly Lys Met Ser Asp Gly Tyr Arg Trp Arg Lys Tyr Gly Gln Lys Ile
                405                 410                 415

Val Lys Gly Asn Pro Asn Pro Arg Ser Tyr Tyr Arg Cys Thr His Asp
            420                 425                 430

Gly Cys Pro Val Arg Lys His Val Glu Lys Ala Pro Asp Asp Xaa Asn
        435                 440                 445

Asn Ile Val Val Thr Tyr Glu Gly Lys His Asn His Asp Gln Pro Phe
    450                 455                 460

Arg Ser Ser Glu Ser Val Asp Gly Pro Val Pro Met Ile Xaa Pro
465                 470                 475                 480

Ala Glu Thr Thr Xaa Glu Gln Pro Ser Thr Xaa Thr Ser Thr Ser Asp
                485                 490                 495

Gln Lys Pro Pro Thr Ser Thr Gln Lys Asp Ala Xaa Xaa Glu Ser Asp
            500                 505                 510

Lys Glu Thr Thr Leu Glu Phe Gly Gly Glu Lys Ala Val Glu Ser Ala
        515                 520                 525

Gln Thr Leu Leu Ser Ile Lys Thr Asn Pro Asp Met Lys Asn Ser
    530                 535                 540

Leu Leu Lys Asp Thr Ser Ala Val Val Pro Val Gln Asn Asn
545                 550                 555

<210> SEQ ID NO 7
<211> LENGTH: 511
<212> TYPE: PRT
<213> ORGANISM: Solanum sp.

<400> SEQUENCE: 7

Met Asp Asp Glu Asn Glu Ser Ser Lys Ser Thr Gly Leu Lys Asn Ser
1               5                   10                  15

Asn Leu Glu Glu Glu Asp Lys Ile Ser Asn Lys Ile Glu Asn Ser
            20                  25                  30

Ser Val His Asn Asp Asp Asn Gly Asp Asp Arg Val Ile Asp Gly Ser
        35                  40                  45

Ser Gly Ala Glu Ser Leu Arg Glu Ser Lys Thr Glu Ala Leu Ile Ser
    50                  55                  60

Glu Thr Leu Ala His Pro Asn Ala Glu Ser Ser Val Gln Ile Glu Ile
65                  70                  75                  80

Asp Gly Gln Ser Glu Phe Asp Ser Glu Phe Ser Pro Ser Tyr Gln Leu
                85                  90                  95

Ser Glu Val Pro Val Glu Tyr Glu Leu Pro Ser Phe Gly Phe Ser Glu
            100                 105                 110
```

```
Lys Ile Lys Asp Arg Ile Ser Val Thr Lys Pro Gly Thr Leu Asn Ala
            115                 120                 125

Gln Ala Arg Thr Glu His Gln Arg Arg Val Pro Asp Ala Ala Ser Ser
        130                 135                 140

Leu Glu Leu Ser Ser Leu Ser Val Ala Gln Ser Ile Ser Ser Val Pro
145                 150                 155                 160

Ser Ala Thr Leu Ala Glu Arg Arg Ser Ala Ala Val Asn Cys Ser
                165                 170                 175

Thr Gly Glu Val Val Lys Gln Ser Ser Asp Ala Gln Val Leu Ala Leu
                180                 185                 190

Val Pro Val Leu Lys Arg Pro Thr Arg Asp Gly Tyr Asn Trp Arg Lys
            195                 200                 205

Tyr Gly Gln Lys Gln Val Lys Ser Pro Gln Gly Ser Arg Ser Tyr Tyr
        210                 215                 220

Arg Cys Thr His Ser Glu Cys Cys Ala Lys Lys Ile Glu Cys Ser Asp
225                 230                 235                 240

His Thr Asn Arg Val Met Glu Ile Ile Tyr Arg Thr Gln His Asn His
                245                 250                 255

Asp Pro Pro Arg Val Asn Cys Pro Arg Glu Ser Lys Ser Ala Leu
            260                 265                 270

Leu Ser Ser Pro Thr Asn Gly Lys Ser Ile Ile Ala His Pro Ser Arg
            275                 280                 285

Asn Ser Ile Glu Thr Val Val Ser Ser Leu Lys Glu Asn Leu Gln Glu
            290                 295                 300

Ser Leu Pro Ile Ala Glu Thr Ala Asn Gln Asp Ser Gly Gly Ser Asp
305                 310                 315                 320

Thr Asp Thr Glu Ile Thr Ile Arg Glu Glu His Arg Asp Glu Ala Gly
                325                 330                 335

Gln Lys Lys Arg Ser Arg Lys Ser Asp Thr Ser Cys Leu Glu Ser Val
            340                 345                 350

Ser Lys Pro Gly Lys Pro Lys Leu Val Val His Ala Ala Cys Asp
            355                 360                 365

Val Gly Ile Ser Ser Asp Gly Tyr Arg Trp Arg Lys Tyr Gly Gln Lys
370                 375                 380

Met Val Lys Gly Asn Pro His Pro Arg Asn Tyr Tyr Arg Cys Thr Ser
385                 390                 395                 400

Ala Gly Cys Pro Val Arg Lys His Ile Glu Arg Val Val Asp Thr Thr
                405                 410                 415

Ser Ala Leu Thr Ile Thr Tyr Lys Gly Val His Asp His Asp Met Pro
                420                 425                 430

Val Pro Lys Lys Arg His Gly Pro Pro Ser Ala Pro Leu Ile Ala Ala
            435                 440                 445

Thr Ala Pro Ala Ser Val Thr Asn Met His Ala Asn Lys Pro Glu Pro
450                 455                 460

Leu Gln His Gln Lys Ser Thr Gln Trp Ser Val Asp Lys Glu Gly
465                 470                 475                 480

Glu Leu Thr Gly Glu Lys Leu Asp Val Gly Gly Glu Lys Ala Met Glu
                485                 490                 495

Ser Ala Arg Thr Leu Leu Ser Ile Gly Phe Glu Ile Lys Pro Cys
                500                 505                 510

<210> SEQ ID NO 8
<211> LENGTH: 513
<212> TYPE: PRT
```

-continued

<213> ORGANISM: Solanum lycopersicum

<400> SEQUENCE: 8

```
Met Asp Asp Glu Asn Glu Ser Ser Lys Ser Ala Gly Leu Lys Asn Ser
1               5                   10                  15

Asn Leu Glu Glu Glu Glu Asp Lys Ile Ser Asn Lys Ile Glu Asn
            20                  25                  30

Ser Ser Val His Asn Asp Glu Asn Gly Asp Asp Arg Val Ile Asp
        35                  40                  45

Gly Ser Ser Gly Ala Glu Ser Leu Arg Glu Ser Lys Thr Gly Ala Leu
    50                  55                  60

Ile Ser Glu Thr Leu Ala His Pro Asn Ala Glu Ser Val Gln Ile
65                  70                  75                  80

Glu Ile Asp Gly Gln Ser Glu Phe Asp Ser Glu Phe Ser Pro Ser Tyr
                85                  90                  95

Gln Leu Ser Glu Val Pro Val Glu Tyr Glu Leu Pro Ser Phe Gly Phe
            100                 105                 110

Ser Glu Lys Ile Lys Asp Arg Ile Ser Val Thr Lys Pro Gly Thr Leu
        115                 120                 125

Asn Ala Gln Ala Arg Thr Glu His Gln Arg Arg Val Pro Asp Ala Ala
130                 135                 140

Ser Ser Leu Glu Leu Ser Ser Leu Ser Val Ala Gln Ser Ile Ser Ser
145                 150                 155                 160

Val Pro Ser Ala Thr Leu Ala Glu Arg Arg Ser Ala Ala Val Asn
                165                 170                 175

Cys Ser Thr Gly Glu Val Val Lys Gln Ser Ser Asp Ala Gln Val Leu
            180                 185                 190

Ala Leu Val Pro Val Leu Lys Arg Pro Thr Arg Asp Gly Tyr Asn Trp
        195                 200                 205

Arg Lys Tyr Gly Gln Lys Gln Val Lys Ser Pro Gln Gly Ser Arg Ser
    210                 215                 220

Tyr Tyr Arg Cys Thr His Ser Glu Cys Cys Ala Lys Lys Ile Glu Cys
225                 230                 235                 240

Ser Asp His Thr Asn Arg Val Met Glu Ile Ile Tyr Arg Thr Gln His
                245                 250                 255

Asn His Asp Pro Pro Arg Val Asn Cys Pro Arg Glu Ser Lys Ser
            260                 265                 270

Ala Leu Leu Ser Ser Pro Thr Asn Gly Lys Ser Ile Ile Ala His Pro
        275                 280                 285

Arg Arg Asn Ser Ile Glu Thr Val Ser Pro Leu Asn Glu Asn Leu
    290                 295                 300

Gln Glu Ser Leu Pro Ile Ala Glu Thr Ala Asn Gln Asp Ser Gly Gly
305                 310                 315                 320

Ser Asp Thr Asp Thr Glu Ile Thr Ile Arg Glu Glu His Arg Asp Glu
                325                 330                 335

Ala Gly Gln Lys Lys Arg Ser Arg Lys Ser Asp Thr Ser Cys Leu Glu
            340                 345                 350

Ser Val Ser Lys Pro Gly Lys Lys Pro Lys Leu Val Val His Ala Ala
        355                 360                 365

Cys Asp Val Gly Ile Ser Ser Asp Gly Tyr Arg Trp Arg Lys Tyr Gly
    370                 375                 380

Gln Lys Ile Val Lys Gly Asn Pro His Pro Arg Asn Tyr Tyr Arg Cys
385                 390                 395                 400
```

```
Thr Ser Ala Gly Cys Pro Val Arg Lys His Ile Glu Arg Val Leu Asp
            405                 410                 415
Thr Thr Ser Ala Leu Thr Ile Thr Tyr Lys Gly Val His Asp His Asp
        420                 425                 430
Met Pro Val Pro Lys Lys Arg His Gly Pro Pro Ser Ala Pro Leu Ile
    435                 440                 445
Ala Ala Thr Ala Pro Ala Ser Val Thr Thr Met His Ala Asn Lys Pro
450                 455                 460
Glu Pro Leu Gln His Gln Lys Ser Thr Thr Gln Trp Ser Val Asp Lys
465                 470                 475                 480
Glu Gly Glu Leu Thr Gly Glu Lys Leu Asp Val Gly Gly Glu Lys Ala
                485                 490                 495
Met Glu Ser Ala Arg Thr Leu Leu Ser Ile Gly Phe Glu Ile Lys Pro
            500                 505                 510
Cys

<210> SEQ ID NO 9
<211> LENGTH: 1533
<212> TYPE: DNA
<213> ORGANISM: Solanum sp.

<400> SEQUENCE: 9
```

| | | | | | |
|---|---|---|---|---|---|
| atggatgacg | aaaacgagag | ctccaaatca | accggactca | aaaattcaaa | tctagaagaa | 60 |
| gaagacaaaa | tcagcaacaa | aatcgaaaat | tcctccgtac | acaacgacga | caacggtgac | 120 |
| gatagagtaa | ttgacggtag | cagtggagct | gagagtttac | gagaatcaaa | gacggaagct | 180 |
| ttaatttcag | aaaccctagc | tcatcctaat | gcagaatcat | ccgtacaaat | tgaaattgat | 240 |
| ggccaatccg | aattcgattc | agagttttct | ccctcttatc | aactttctga | agtaccagtg | 300 |
| gaatatgaac | tgccctcgtt | tggtttctcg | aaaaaaatca | aggatagaat | tagtgttacc | 360 |
| aaacctggaa | ctttgaatgc | tcaagcacga | acagaacatc | aacgacgtgt | tcctgatgca | 420 |
| gcatcctcat | tggagctgtc | ctctttatct | gttgcacagt | ccatttcatc | agtgccaagt | 480 |
| gcaactctag | cagaaagacg | atcagcagca | gcagtaaatt | gtagtacagg | agaagtggtt | 540 |
| aagcagagtt | ctgacgccca | ggttctagct | cttgtaccag | ttctaaagag | accaactcgc | 600 |
| gatgggtaca | attggcggaa | gtatggtcaa | aagcaagtta | aaagtcctca | aggttctcga | 660 |
| agttattacc | gatgcactca | ttctgagtgt | tgtgccaaga | agattgagtg | ctctgatcac | 720 |
| actaatcgtg | ttatggagat | tatttataga | actcaacaca | atcatgatcc | accccaaga | 780 |
| gtaaattgcc | caagggaaag | caagtctgca | ttattgtctt | cacctaccaa | tgcaaaagt | 840 |
| ataatagctc | atccaagtag | aaattctatt | gagaccgtag | tatcctcctt | aaaagaaaat | 900 |
| ttgcaagaaa | gtttaccaat | tgctgagaca | gcaaatcagg | attccggtgg | gtctgacact | 960 |
| gacactgaaa | tcactattag | agaggagcac | cgtgacgagg | ctggacaaaa | gaagaggtca | 1020 |
| aggaaaagtg | acacaagttg | tttggaatct | gtttctaaac | ctggaaagaa | acccaagctt | 1080 |
| gtggtgcatg | ctgcttgtga | tgtaggaatc | tcaagtgatg | gctacagatg | gcgaaagtat | 1140 |
| ggacaaaaaa | tggtgaaggg | aaatcccccat | ccaaggaact | actatcgctg | tacatcagct | 1200 |
| ggatgtcctg | ttcgaaagca | cattgagagg | gttgtagata | ccacaagtgc | tttaacaata | 1260 |
| acatacaagg | gagtacacga | tcatgacatg | ccagtaccca | aaaaacgtca | tggtccaccg | 1320 |
| agtgcacctc | ttattgctgc | tactgcccct | gcttccgtaa | ccaatatgca | tgctaacaaa | 1380 |
| cccgaaccgc | tacaacatca | aaaatcgacc | acacaatggt | ccgtggacaa | agaaggtgag | 1440 |

```
ttgactggtg agaaattgga tgttggagga gaaaaagcaa tggaatcggc tcgaactctg    1500
ttgagtattg gatttgaaat taagccttgc taa                                 1533

<210> SEQ ID NO 10
<211> LENGTH: 6185
<212> TYPE: DNA
<213> ORGANISM: Solanum lycopersicum

<400> SEQUENCE: 10 cattttttc acaaaaacac tcactgtgtg ttcatcggaa tccgccatgg atgacgaaaa      60
cgagagctcc aaatcagccg gactcaaaaa ttcaaatcta gaagaagaag aagaagataa    120
aatcagcaac aaaatcgaaa attcctccgt acacaacgac gaaaacggtg acgacgatag    180
agtaattgac ggtagcagtg gagctgagag tttacgagaa tcaaagacgg gagctttaat    240
ttcagaaacc ctagctcatc ctaatgcaga atcatccgta caaattgaaa ttgatggcca    300
atccgaattc gattcagagt tttctccctc ttatcaactt tctggtacta ttcaatgccg    360
tttaattcgt tcttatgctt ttttttgtg tgtgaaattg agtagttcat gtttcatttt     420
ttatgatcaa tttctataca tttgaaccat ttttttata atcttgtatc cctataacga     480
ctctgctaat tccacgagat atctgtttcg ttccacgagc gtattaagta acttgtataa    540
catgagaaaa aaaatacaat ttatgtgaca tgatatcgtt ttttagtagg ttctatagaa    600
aaggacacat ttttattatt tagtaacaac ttaatgttaa gatatatctt cacccttagt    660
gagaagtttc aaaagtgttc tttttaacat cgcgtaaatt gggatgaaga agtagtagt     720 attttgtctc tgctgggaat tgaacgtgag atttacgat gcttaacatc ttcattgacg     780
gctaagccac acacttgggt gctatacttt tgaatttctt tcctgtttta tgtgtatata    840
agcgtagaat gtttagttgt tgatcaaaag cacaccgaaa gtattatgac tagttttccgt   900 attaggtgtt caccttctca ttcgaccacc tatcaccaat tgttcacaca cgtgttacga    960
taaatagttg atgattgttc aaatagaaaa ggaaaacacc tcaactatca tttgtgagtc   1020
tcatggtcaa ggtgtgttttt atactaacgg acatacacgt gttataatat tatccaccga  1080
cttgacattt ataaaatatt agatcgataa tgaagattgt gccacgtgtc cctgtaagta   1140
tagcaaacgg tatatgcata ccatttatga tagtttgggg tatatttgtc ctttttcccg   1200
taataaatac ttggtggtag tttacgtaga aaaagtgaac accgaatagt tcatataggg   1260
aatttgcaaa aagatcttca ggtgcgtttg gccattatat ctaggaggca agtccttttg   1320
attttatatt tttgtgtaag agagattatg atcatgagtt ctccttatca aaagaaata    1380 aattatgatc atgagtttta tgagttttta agtagaaaaa gggaataagt tatacttgag   1440
gtgtgttttg acaaatagtc gttaatagat cagataggaa aactgaacat ctaatagttc   1500 ataggaaa cttgcaaaaa tgtgatactt cacgtgtatt ttgaccatta tatctggaat     1560
gtaagtcctt ttgagttgta catgcatgct taattgtcta cgaaaattct gtaattattg   1620
tgttgaataa tctggcagaa gtaccagtgg aatatgaact gccctcgttt ggtttctcgg   1680
aaaaaatcaa ggtatgcagt tccttctctt tgacttggta tttaattttg ttatgatagt   1740
ttatctattt cgagatgtgg gagatggttg agtggattcg atgtggtagc atattcttat   1800
tatattgtag agggagcata cgcactaccc tccctggacc ccacttatcg gattagagtg   1860
gttatgttgt tgtattttaa taagttagtt tttcaattat cttgttacta taatcatagg   1920
tgtcaatgta tctgaatagt acttactcaa aaaagaaaaa acaagtagtg tatttgaatg   1980
gtagcacaga gatactgagg taatttacga taggggtgga caacatgcgc aagtagaaaa   2040
```

```
ttcaaggtga ttgctctgtc actatttgga gttttggacc ggagagctcg ctgctttttt    2100
ttagtagata tgtacaaggt cgattagaat acagaagtta aattctgcta aagctgaaac    2160
ttaagtgtca gtataaatcg agccaaaaat ttctgcaata taaatcactg aggtttctgg    2220
agttattgtg gtaaacaggg tgcatgatta tcggttctac aagattctat gcacattcca    2280
tgttgcatat acaaagttat tctgaagatt tagaagttct tgtttatcct catttgcgtt    2340
ttatgaagca tgcgacaaag tagttttgtc ttaaaagatc aagttaggta ggagttgaaa    2400
atggagtaga gtgtcctcgt acacctcctt attcatgatg gttgatattg gaatcgtta     2460 gtaggtgatg ggcagtctgt agaaatacgt tgagctgatg tgtggcatga gcttgagata    2520
tcacatacac ggtgatgggt attgtaactg taaatttaga cgttttctct gagagagcta    2580
tataagggtc tgatttaaat gtagtaaccc catcatattt atgaagcctc taagaacagt    2640
gttttgggaa gcgagaagcg gaaaaagcg atgagggttc gctttacaga aggcgatatt     2700
tagtataaaa ataaaattat ataaattaac tgaatagagg taatatattc ttagattata    2760
agaaaataga tagtcaataa tacttataag tcataacata taaagcaaaa aaatcaaaaa    2820
cataattaaa tcacaaagaa tcaaactcct actcttcaac aagatcctca aactctttaa    2880
aatgcagcaa taaaaatata aaaaaacacc cagcagtaac caaaaaaaaa aacaagtagc    2940
agatagcagc agcttcgtag agaagaagag aagaagaaaa aaaaacttac agaagcttgg    3000
cagcaaccaa ccaaaaagag tatgaagaag agaagaagaa gagaacttgc ataaaaaaaa    3060
gtctgaagaa gagaagaaga agagaacttg cataaaaaaa agtctgaaga agagaagaag    3120
aagagaactt gcataaaaaa aagtctgaag aagagaagca gtcgcagctg tgagtgaagt    3180
cgcgacagat ggaaagagta tgtgaagtcg catatctttc tgaaattaaa aaaaaaaact    3240
tacaattttt ttggaaaaaa aacataaggg gcgctttta tgctttatcg cgctttcgtt     3300
tttctggcgc ttctcgcttc tacagtagaa gcgagcgcct tttcaatgtc accttgcctc    3360
aggagctaaa agcgcaagag catcgcctca ctttaagcgc gcttttcaca acactgtcta    3420
agacataccg aaaggcttaa atgcacgaga taagataact cagagatgat ggcctaggct    3480
cgaacttgtg acttaaccgg gggcgggtgg tggtggaaag gggactatat cattactata    3540
ccagtgtgag gcatagttgt tttgtgcatt agattttgtt tcctaaatga gcaatgaagt    3600
gggtgcaaac cttggagaat accagtagag acaaaaaaac actaggtgtt ttcccatctg    3660
tctgagcctt agggttatag ttatccggta ctcatgttgg tggataatac tcaagtagca    3720
ggtaccgctt gaggaatcat catgatcctt tagttttgga taaattgaaa gcagatgcaa    3780
gaaaccttaa caattgtcat atggtgacca tcacatggcc actctaactc ataatatctc    3840
atattgcaac attattttg acgtgatgct ataaataatt aatagtccaa ttatgtttgt      3900
aggttaatac attcattttt ccagagtatc tggtttcgac ttttctgttt ataataatgt    3960
tttacttttt actgaaaagt ttatacagaa ttgctggaac tggatatgta tatttgtggg    4020
atggaacaaa tgagtcattt catgttgtat gcaggataga attagtgtta ccaaacctgg    4080
aactttgaat gctcaagcac gaacagaaca tcaacgacgt gttcctgatg cagcatcctc    4140
attggagctg tcctctttat ctgttgcaca gtccatttca tcagtgccaa gtgcaactct    4200
agcagaaaga cgatcagcag cagcagtaaa ttgtagtaca ggagaagtgg ttaagcagag    4260
ttctgacgcc caggttctag ctcttgtacc agttctaaag agaccaactc gcgatgggta    4320
caattggcgg aagtatggtc aaaagcaagt taaaagtcct caaggttctc gaagttatta    4380
```

-continued

```
ccgatgcact cattctgagt gttgtgccaa gaagattgag tgctctgatc acactaatcg    4440
tgttatggag attatttata gaactcaaca caatcatgat ccaccccaa gagtaaattg     4500 cccaagggaa agcaagtctg cattattgtc ttcacctacc aatggcaaaa gtataatagc   4560
tcatccaagg agaaattcta ttgagaccgt agtatccccc ttaaatgaaa atttgcaaga   4620
aagtttacca attgctgaga cagcaaatca ggattcaggt gggtctgaca ctgacactga   4680
aatcactatt agagaggagc accgtgacga ggctggacaa agaagagagc aagttcactt   4740
ttgtattcaa ttttagttat tttatttttc tgcttttcct cttacaaatg ttcaaaacca   4800
tatgattgat caccattctc acctatgatt ttcaggtcaa ggaaaagtga cacaagttgt   4860
ttggaatctg tttctaaacc tggaaagaaa cccaagcttg tggtgcatgc tgcttgtgat   4920
gtaggaatct caagtgatgg ctacagatgg cgaaagtatg acaaaaaat agtgaaggga    4980 aatccccatc caaggtactg tattattttc tgccgtacac ttgataaatc gtttgattgt   5040
tctgcctgcc ttacgctgaa attataagaa ctaggaggga gtgatgccac attaaacaca   5100
tttcttgaat catacttggg agttttttt tctctattt ctctgctttg tttccttttg     5160
ttggattgtg ctgatggatg agttctattc ttcatgcacc ctattctgct ctgttaaact   5220
aagttgctcg gactcttcaa aaatgttgat gggtgcatga gggatactcc aacagtagtg   5280
cattttcaga gaatccaaca cgggtgcagc agcattttgg agactccgag caacatagtt   5340
gttaaatgct atggatgaga gtgtcactca tcttattccc ttttctgttc tgttaagaca   5400
attaggtttt cttcaggtaa ataattcctg ctagttttct gtttcaagtt agaatttctt   5460
atgattcaac atcaatattg acaactcttc tcacatatta cttgttttta tctacttcac   5520
gttttaactc atatcttggt caaaagtata cttcattttg cttctttcgt tctcctgttc   5580
tgtcctgagt tgtttcctgg atgaccttta ggaactacta tcgctgtaca tcagctggat   5640
gtcccgttcg aaagcacatt gagagggttt tagataccac aagtgcttta acaataacat   5700
acaagggagt acacgatcat gacatgccag tacccaaaaa acgtcatggt ccaccgagtg   5760
cacctcttat tgctgctact gcccctgctt ccgtaaccac tatgcatgct aacaaacccg   5820 aaccccctaca acatcaaaaa tcgaccacac aatggtccgt ggacaaagaa ggtgagttga   5880
ctggtgagaa attggatgtt ggaggagaaa aagcaatgga atcggctcga actctattga   5940
gtattggatt tgaaattaag ccttgctaaa attgcttagc tgctctgatt ttattttttt   6000
ctgcatttat ttagttttcc tccatagggc tttcttgtag aagtttagaa gagtacacct   6060
ttttttttat agtcctccaa tatatagatg gtctatactc agttatgtac attattgtgg   6120
atcaaaataa gtaacataga acttagaata acatattgtg atgtttgtca atttgcatct   6180
gtttc                                                               6185
```

<210> SEQ ID NO 11
<211> LENGTH: 1542
<212> TYPE: DNA
<213> ORGANISM: Solanum lycopersicum

<400> SEQUENCE: 11

```
atggatgacg aaaacgagag ctccaaatca gccggactca aaaattcaaa tctagaagaa     60
gaagaagaag ataaaatcag caacaaaatc gaaaattcct ccgtacacaa cgacgaaaac   120
ggtgacgacg atagagtaat tgacggtagc agtggagctg agagtttacg agaatcaaag   180
acgggagctt taatttcaga aaccctagct catcctaatg cagaatcatc cgtacaaatt   240
gaaattgatg ccaatccga attcgattca gagttttctc cctcttatca actttctgaa   300
```

```
gtaccagtgg aatatgaact gccctcgttt ggtttctcgg aaaaaatcaa ggatagaatt      360
agtgttacca aacctggaac tttgaatgct caagcacgaa cagaacatca acgacgtgtt      420
cctgatgcag catcctcatt ggagctgtcc tctttatctg ttgcacagtc catttcatca      480
gtgccaagtg caactctagc agaaagacga tcagcagcag cagtaaattg tagtacagga      540
gaagtggtta agcagagttc tgacgcccag gttctagctc ttgtaccagt tctaaagaga      600
ccaactcgcg atgggtacaa ttggcggaag tatggtcaaa agcaagttaa aagtcctcaa      660
ggttctcgaa gttattaccg atgcactcat tctgagtgtt gtgccaagaa gattgagtgc      720
tctgatcaca ctaatcgtgt tatggagatt atttatagaa ctcaacacaa tcatgatcca      780
cccccaagag taaattgccc aagggaaagc aagtctgcat tattgtcttc acctaccaat      840
ggcaaaagta taatagctca tccaaggaga aattctattg agaccgtagt atcccccta      900 aatgaaaatt tgcaagaaag tttaccaatt gctgagacag caaatcagga ttcaggtggg      960
tctgacactg acactgaaat cactattaga gaggagcacc gtgacgaggc tggacaaaag     1020
aagaggtcaa ggaaaagtga cacaagttgt ttggaatctg tttctaaacc tggaaagaaa     1080
cccaagcttg tggtgcatgc tgcttgtgat gtaggaatct caagtgatgg ctacagatgg     1140
cgaaagtatg gacaaaaaat agtgaaggga atccccatc caaggaacta ctatcgctgt     1200
acatcagctg gatgtcccgt tcgaaagcac attgagaggg ttttagatac acaagtgct     1260 ttaacaataa catacaaggg agtacacgat catgacatgc cagtacccaa aaaacgtcat     1320
ggtccaccga gtgcacctct tattgctgct actgcccctg cttccgtaac cactatgcat     1380
gctaacaaac ccgaacccct acaacatcaa aaatcgacca cacaatggtc cgtggacaaa     1440
gaaggtgagt tgactggtga gaaattggat gttggaggag aaaaagcaat ggaatcggct     1500
cgaactctat tgagtattgg atttgaaatt aagccttgct aa                        1542

<210> SEQ ID NO 12
<211> LENGTH: 201
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
ctgacatgcc agtacccaaa aaacgtcatg gtccaccgag tgcacctctt attgctgcta       60
ctgcccctgc ttccgtaacc actatgcatg ctaacaaacc cgaacccta caacatcaaa      120 aatcgaccac acaatggtcc gtggacaaag aaggtgagtt gactggtgag aaattggatg      180
ttggaggaga aaaagcaatg g                                                201

<210> SEQ ID NO 13
<211> LENGTH: 2229
<212> TYPE: DNA
<213> ORGANISM: Arabidopsis thaliana

<400> SEQUENCE: 13
ttttcttccg gagatcagtc ggtcggaaag cggctaccct tttgtctgcc tagagaattt       60
gttcgtttct ttcttttact ctcttcagac aaaacccacg agatacagaa aaagaggaca      120
agagagaatc gtccatggaa gaagacactg gtatcgacga agctaagaca tacacggtgg      180
agaagagcga gaaagtggag ccggagaagg acggactgag tcaattcaga gacgaggaaa      240
aatcacttgg tgcggatatg gaagatttac atgatgagac tgtgcgagaa accctaggca      300
```

```
aggatcaggt tcaaggtaac ggtttattct gcgcaaaatt ctttattggt ttttatttat    360
ttattcgaga ctttatttt tgacgaaatg atgtttgagt ttaccaggtg ttcgagaaaa    420
ttcctctgtg gaaccaaatg ttgaagatgt attagaagtg aatgtgagtt tgcttcagac    480
tcttctgcta ttcataaact ttcttaacac ttacaacttt gattctctca ttaacattga    540
ttgtgctaga acttgtaaag tttaactcat ttcagtgtct tcgatgttac tcgttcagtg    600
attatacaat aacatgggaa taggattaat cgtaatggtt ttaacctttg gccaagttca    660
atctgtatct gtatcagttt gatctgttac attttagtgt gtctgatttc ttaggcaatt    720
ctgaggacaa gaatcactgt tatcaaggca tgacatttaa ctgcttttg tatcacattg     780 gcaggagact gatagcgtca aggaaactgt tgtaagtgcg attgtgccgg ttgatgaagt    840
ggaagagaat cgtcaggtag aaacatctcc ttctctggct gcatcgtcag actcattgac    900
agtgacgcca tgtctatctt tggatcctgc aactgcttca accgcacaag atttaccact    960
ggtttcagtt ccaactaaac aagagcaaag atcagattcg ccggtggtta acagattgtc   1020
ggttactcct gttcctagga caccggctcg tgatggttat aattggagaa atatggaca    1080 gaagcaggtt aagagtccca agggctcacg gagttactac aggtgtacat acactgaatg   1140
ttgtgctaaa aaaattgaat gctccaatga ttcaggcaat gtggtagaga ttgttaacaa   1200
aggtttacat actcatgaac ctccccggaa gactagcttc tccccgagag agattagagt   1260
tacaacagct atccggcctg tttcagagga tgatacagta gtagaagagc tatcaattgt   1320
tcctagcggt tcagatccgt ctgcttctac taaagaatac atctgtgagt cgcaaacact   1380
cgttgaccgg aaaagacact gtgagaacga agctgtggag gaaccagagc caaaacgaag   1440
gcaagtttgt agaattttgc atttcggtgc ttactcttca ctttgaaaga tgaaattaat   1500
agactttctt ctctctatt ttcagactga aaaagataa ctcacagagt tcagattctg    1560
tctccaaacc tggaaagaaa aacaaattcg tagtacacgc agctggtgat gttggtatct   1620
gtggtgatgg atacaggtgg cgtaaatacg ggcagaaaat ggtgaaagga atcctcatc    1680 caaggtctag aaaactaaac gcatgaccca tctctttatc cacatatgac atcttctaat   1740
acgcatggtg attgatttgt tctgtttcaa acattcagga actactaccg atgcacttca   1800
gcgggatgtc cagttcgtaa acacattgag acagcagtcg agaacacaaa agcagtaata   1860
atcacataca aaggagtaca caaccacgac atgccggtgc ctaagaaacg ccatggtcct   1920
ccaagctcaa tgctcgtagc tgcagccgct ccaacatcaa tgagaaccag gacagacgat   1980
caggtgaaca ttccgacttc aagccagtgc tcggtggggc gagaaagtga gaagcagagt   2040
aaagaagcat tggacgttgg tggagagaaa gtgatggaat cagctaggac tttgttgagc   2100
attggattcg aaatcaagca atgctgatta tatgtagttt atgagttta tagagttcat    2160 cgactcaatt ttcgcctcct tgttcttgtt atataataat aataaaaaac cccatgaaga   2220
ttaccaact                                                           2229

<210> SEQ ID NO 14
<211> LENGTH: 1401
<212> TYPE: DNA
<213> ORGANISM: Arabidopsis thaliana

<400> SEQUENCE: 14
atggaagaag acactggtat cgacgaagct aagacataca cggtggagaa gagcgagaaa     60
gtggagccgg agaaggacgg actgagtcaa ttcagagacg aggaaaaatc acttggtgcg    120
```

```
gatatggaag atttacatga tgagactgtg cgagaaaccc taggcaagga tcaggttcaa        180
ggtgttcgag aaaattcctc tgtggaacca aatgttgaag atgtattaga agtgaatgag        240
actgatagcg tcaaggaaac tgttgtaagt gcgattgtgc cggttgatga agtggaagag        300
aatcgtcagg tagaaacatc tccttctctg gctgcatcgt cagactcatt gacagtgacg        360
ccatgtctat ctttggatcc tgcaactgct tcaaccgcac aagatttacc actggtttca        420
gttccaacta acaagagca aagatcagat tcgccggtgg ttaacagatt gtcggttact        480
cctgttccta ggacaccggc tcgtgatggt tataattgga gaaaatatgg acagaagcag        540
gttaagagtc ccaagggctc acggagttac tacaggtgta catacactga atgttgtgct        600
aaaaaaattg aatgctccaa tgattcaggc aatgtggtag agattgttaa caaaggttta        660
catactcatg aacctccccg gaagactagc ttctccccga gagagattag agttacaaca        720
gctatccggc ctgtttcaga ggatgataca gtagtagaag agctatcaat tgttcctagc        780
ggttcagatc cgtctgcttc tactaaagaa tacatctgtg agtcgcaaac actcgttgac        840
cggaaaagac actgtgagaa cgaagctgtg gaggaaccag agccaaaacg aagactgaaa        900
aaagataact cacagagttc agattctgtc tccaaacctg gaaagaaaaa caaattcgta        960
gtacacgcag ctggtgatgt tggtatctgt ggtgatggat acaggtggcg taaatacggg       1020
cagaaaatgg tgaaaggaaa tcctcatcca aggaactact accgatgcac ttcagcggga       1080
tgtccagttc gtaaacacat tgagacagca gtcgagaaca caaaagcagt aataatcaca       1140
tacaaaggag tacacaacca cgacatgccg gtgcctaaga aacgccatgg tcctccaagc       1200
tcaatgctcg tagctgcagc cgctccaaca tcaatgagaa ccaggacaga cgatcaggtg       1260
aacattccga cttcaagcca gtgctcggtg gggcgagaaa gtgagaagca gagtaaagaa       1320
gcattggacg ttggtggaga aaagtgatg gaatcagcta ggactttgtt gagcattgga       1380
ttcgaaatca agcaatgctg a                                                1401
```

<210> SEQ ID NO 15
<211> LENGTH: 466
<212> TYPE: PRT
<213> ORGANISM: Arabidopsis thaliana

<400> SEQUENCE: 15

```
Met Glu Glu Asp Thr Gly Ile Asp Glu Ala Lys Thr Tyr Thr Val Glu
1               5                   10                  15

Lys Ser Glu Lys Val Glu Pro Glu Lys Asp Gly Leu Ser Gln Phe Arg
            20                  25                  30

Asp Glu Glu Lys Ser Leu Gly Ala Asp Met Glu Asp Leu His Asp Glu
        35                  40                  45

Thr Val Arg Glu Thr Leu Gly Lys Asp Gln Val Gln Gly Val Arg Glu
    50                  55                  60

Asn Ser Ser Val Glu Pro Asn Val Glu Asp Val Leu Glu Val Asn Glu
65                  70                  75                  80

Thr Asp Ser Val Lys Glu Thr Val Val Ser Ala Ile Val Pro Val Asp
                85                  90                  95

Glu Val Glu Glu Asn Arg Gln Val Glu Thr Ser Pro Ser Leu Ala Ala
            100                 105                 110

Ser Ser Asp Ser Leu Thr Val Thr Pro Cys Leu Ser Leu Asp Pro Ala
        115                 120                 125

Thr Ala Ser Thr Ala Gln Asp Leu Pro Leu Val Ser Val Pro Thr Lys
    130                 135                 140
```

-continued

```
Gln Glu Gln Arg Ser Asp Ser Pro Val Val Asn Arg Leu Ser Val Thr
145                 150                 155                 160

Pro Val Pro Arg Thr Pro Ala Arg Asp Gly Tyr Asn Trp Arg Lys Tyr
                165                 170                 175

Gly Gln Lys Gln Val Lys Ser Pro Lys Gly Ser Arg Ser Tyr Tyr Arg
            180                 185                 190

Cys Thr Tyr Thr Glu Cys Cys Ala Lys Lys Ile Glu Cys Ser Asn Asp
        195                 200                 205

Ser Gly Asn Val Val Glu Ile Val Asn Lys Gly Leu His Thr His Glu
    210                 215                 220

Pro Pro Arg Lys Thr Ser Phe Ser Pro Arg Glu Ile Arg Val Thr Thr
225                 230                 235                 240

Ala Ile Arg Pro Val Ser Glu Asp Asp Thr Val Val Glu Glu Leu Ser
                245                 250                 255

Ile Val Pro Ser Gly Ser Asp Pro Ser Ala Ser Thr Lys Glu Tyr Ile
                260                 265                 270

Cys Glu Ser Gln Thr Leu Val Asp Arg Lys Arg His Cys Glu Asn Glu
            275                 280                 285

Ala Val Glu Glu Pro Glu Pro Lys Arg Arg Leu Lys Lys Asp Asn Ser
        290                 295                 300

Gln Ser Ser Asp Ser Val Ser Lys Pro Gly Lys Lys Asn Lys Phe Val
305                 310                 315                 320

Val His Ala Ala Gly Asp Val Gly Ile Cys Gly Asp Gly Tyr Arg Trp
                325                 330                 335

Arg Lys Tyr Gly Gln Lys Met Val Lys Gly Asn Pro His Pro Arg Asn
            340                 345                 350

Tyr Tyr Arg Cys Thr Ser Ala Gly Cys Pro Val Arg Lys His Ile Glu
        355                 360                 365

Thr Ala Val Glu Asn Thr Lys Ala Val Ile Ile Thr Tyr Lys Gly Val
    370                 375                 380

His Asn His Asp Met Pro Val Pro Lys Lys Arg His Gly Pro Pro Ser
385                 390                 395                 400

Ser Met Leu Val Ala Ala Ala Pro Thr Ser Met Arg Thr Arg Thr
                405                 410                 415

Asp Asp Gln Val Asn Ile Pro Thr Ser Ser Gln Cys Ser Val Gly Arg
            420                 425                 430

Glu Ser Glu Lys Gln Ser Lys Glu Ala Leu Asp Val Gly Gly Lys
        435                 440                 445

Val Met Glu Ser Ala Arg Thr Leu Leu Ser Ile Gly Phe Glu Ile Lys
    450                 455                 460

Gln Cys
465

<210> SEQ ID NO 16
<211> LENGTH: 4
<212> TYPE: PRT
<213> ORGANISM: Unknown
<220> FEATURE:
<223> OTHER INFORMATION: Description of Unknown:
      WRKY domain sequence

<400> SEQUENCE: 16

Trp Arg Lys Tyr
1

<210> SEQ ID NO 17
```

```
<211> LENGTH: 33
<212> TYPE: PRT
<213> ORGANISM: Unknown
<220> FEATURE:
<223> OTHER INFORMATION: Description of Unknown:
      C2H2 zinc finger sequence
<220> FEATURE:
<221> NAME/KEY: MOD_RES
<222> LOCATION: (2)..(6)
<223> OTHER INFORMATION: Any amino acid
<220> FEATURE:
<221> NAME/KEY: MISC_FEATURE
<222> LOCATION: (2)..(6)
<223> OTHER INFORMATION: This region may encompass 4-5 residues
<220> FEATURE:
<221> NAME/KEY: MOD_RES
<222> LOCATION: (8)..(30)
<223> OTHER INFORMATION: Any amino acid
<220> FEATURE:
<221> NAME/KEY: MISC_FEATURE
<222> LOCATION: (8)..(30)
<223> OTHER INFORMATION: This region may encompass 22-23 residues
<220> FEATURE:
<221> NAME/KEY: MOD_RES
<222> LOCATION: (32)..(32)
<223> OTHER INFORMATION: Any amino acid

<400> SEQUENCE: 17

Cys Xaa Xaa Xaa Xaa Xaa Cys Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa His Xaa
            20                  25                  30

His

<210> SEQ ID NO 18
<211> LENGTH: 35
<212> TYPE: PRT
<213> ORGANISM: Unknown
<220> FEATURE:
<223> OTHER INFORMATION: Description of Unknown:
      C2HC zinc finger sequence
<220> FEATURE:
<221> NAME/KEY: MOD_RES
<222> LOCATION: (2)..(8)
<223> OTHER INFORMATION: Any amino acid
<220> FEATURE:
<221> NAME/KEY: MOD_RES
<222> LOCATION: (10)..(32)
<223> OTHER INFORMATION: Any amino acid
<220> FEATURE:
<221> NAME/KEY: MOD_RES
<222> LOCATION: (34)..(34)
<223> OTHER INFORMATION: Any amino acid

<400> SEQUENCE: 18

Cys Xaa Xaa Xaa Xaa Xaa Xaa Xaa Cys Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

His Xaa Cys
        35
```

NEMATODE RESISTANCE

CROSS-REFERENCE TO RELATED APPLICATIONS

This application is the National Phase of International Patent Application No. PCT/NL2017/050400, filed Jun. 16, 2017, published on Dec. 21, 2017 as WO 2017/217852 A1, which claims priority to NL Patent Application No. 2016980, filed Jun. 16, 2016. The contents of these applications are herein incorporated by reference in their entirety.

SEQUENCE LISTING

The instant application contains a Sequence Listing which has been filed electronically in ASCII format and is hereby incorporated by reference in its entirety. Said ASCII copy, created on Aug. 12, 2019, is named 085342-2900_SL.txt and is 69,185 bytes in size.

FIELD OF THE INVENTION

The invention is in the field of agriculture, in particular in the field of crop protection, more particularly in the field of providing nematode resistance to plants.

BACKGROUND OF THE INVENTION

Plant-parasitic nematodes infect a large number of agricultural crops around the world (Baum et al. 2007, Genetic Engineering Vol. 28, Ed. J. K. Setlow, page 17; Jones et al. 2013, Molecular Plant Pathology Vol 14(9), page 946). Root-knot nematodes (*Meloidogyne* spp.) and cyst nematodes (*Heterodera* and *Globodera* spp.) are the most economically relevant plant-parasitic nematodes, causing very substantial losses per year (Rahman et al. 2013, Journal of Environmental Science and Health Part B Vol 48, page 16; Hewezi and Baum 2013, MPMI Vol 26(1), page 9). After penetration and migration through the root, root-knot nematodes induce modification of host cells into specialized feeding structures (giant cells, embedded within galls) from which they feed and develop throughout their life cycle. These giant cells drain nutrients from the plant (Grunder and Hofmann 2011, Genomics and Molecular Genetics of Plant-Nematode Interactions, Ed. J. Jones, page 423). Root dysfunction is the main problem caused by nematodes in crop production, leading to reduced rooting volume and inefficient water and nutrient utilization.

In crop production, nematode infections are battled using a number of practices, including crop rotation, heavy use of nematicides, and genetic crop resistance. The use of nematicides has been dramatically reduced world-wide due to concerns about: i. human health, ii. food safety due to residual chemicals in food crops, and iii. effects on non-target organisms and negative impact on ecosystems (Haydock et al. 2013, Plant Nematology, Ed. R. Perry and M. Moens, $2^{nd}$ edition, page 459). Therefore, there is a high demand for alternative solutions to protect crops from damage by nematodes. In many crops, resistance to nematodes is found in wild accessions and such resistance can be incorporated into elite material through crossing and selection. Nevertheless, there is only a small basis of genetic resistance to nematodes in most crops, including tomato. Wide-spread use of such genetic host resistance exerts selection pressure onto nematode populations resulting in resistance-breaking isolates (Davies and Elling 2015, Nematology Vol 17, page 249).

In tomato, root-knot nematodes have been long dealt with using a resistance gene called Mi1.2 derived from *S. peruvianum*, but in recent years several *Meloidogyne* species, including *M. incognita*, have been identified that are unaffected by Mi1.2-mediated resistance in tomato. Hence, there is an urgent need for new genetic solutions in a number of crop species to ensure durable resistance to plant pathogenic nematodes.

As obligate biotrophic parasites, root-knot nematodes rely on the cells of the feeding structure as a source of nutrients to complete their life cycle (Kyndt et al. 2012, New Phytologist Vol 196, page 887). Thus, root-knot nematodes cause little or no necrosis on root cells since they migrate intercellularly (between cells), in contrast to cyst nematodes, which migrate intracellularly (through cells). In root-knot nematodes, the formation of feeding cells is induced by single second-stage juvenile (J2) nematodes that have the ability to re-program pro-vascular cells into giant cells, by stimulating division of the cell nucleus and cell expansion (Jones and Goto 2011, Genomics and Molecular Genetics of Plant-Nematode Interactions, Ed. J. Jones, page 83). The nematode specifically selects cells that will become its host feeding structure, typically by inducing the formation of four to six giant cells. One of the first signs of giant cell formation is stimulated cell division and the appearance of bi-nucleate cells, which result from the failure to form the cell plate between the two daughter nuclei. After the formation of the feeding structure, the nematode becomes sedentary and is surrounded by a gall (a voluminous root structure formed by cell hyperplasia), which is visible 24 h after infection. Cell re-programming is needed to induce the formation of the feeding structures. This results from an altered state of gene expression in the host that is induced by the nematodes (Bellafiore and Biggs 2010, Current Opinion in Plant Biology Vol 13, page 442). Some of the host gene products, that promote or facilitate the establishment of nematodes and support their development, act as host susceptibility factors.

Upon infection, transcriptomic changes in the host ultimately lead to the successful invasion, establishment and development of invading nematodes. During a compatible interaction, these changes in gene expression are key to preparing the host as a suitable environment for the nematodes to settle and reproduce (Gheysen and Mitchum 2011, Current Opinion in Plant Biology Vol 14, pages 415-421). However, it remains elusive how, and what gene(s) or modification(s) in gene expression lead to the successful invasion, establishment and development of invading nematodes (e.g. root-knot and/or cyst nematode) in a plant. It is also unclear how and what gene(s) or modification(s) in gene expression can be targeted or altered or reversed in a plant so as to prevent or reduce the successful invasion, establishment and development of invading nematodes in said plant.

Thus, there remains a need in the art to uncover new molecular target(s) (e.g. genes) and their related protein(s), which can be manipulated or altered in a plant to prevent or reduce the successful invasion, establishment and development of invading nematodes (e.g. root-knot and/or cyst nematodes) in said plant. There is also a need for alternative or improved methods for conferring nematode resistance to a plant relying on the use of such molecular target(s), thereby allowing efficient generation of plants resistant to nematodes or having an improved nematode resistance compared to a control plant, e.g., a wildtype plant.

SUMMARY OF THE INVENTION

The present invention provides a method for producing a plant having improved nematode resistance compared to a control plant, comprising the step of impairing the expression and/or the activity of a WRKY32 polynucleotide or polypeptide in said plant.

The invention also relates to a method for producing a plant having improved nematode resistance compared to a control plant, comprising the step of impairing expression and/or activity of a polypeptide comprising an amino acid sequence of any of SEQ ID NO: 1, 2, 3, 4, 5, 6, 7, 8 or 15 or a variant thereof having at least 80%, more preferably at least 90%, even more preferably at least 95%, most preferably at least 98% or 99% sequence identity to the amino acid sequence of any of SEQ ID NO: 1, 2, 3, 4, 5, 6, 7, 8 or 15, in a plant cell, plant part or plant, and optionally regenerating said plant.

The invention further provides for a method for producing a plant having improved nematode resistance compared to a control plant, comprising the step of impairing the expression of a polynucleotide encoding a polypeptide comprising the amino acid sequence of any of SEQ ID NO:1, 2, 3, 4, 5, 6, 7, 8 or 15, or a variant thereof having at least 80%, more preferably at least 90%, even more preferably at least 95%, most preferably at least 98% or 99% sequence identity to the amino acid sequence of any of SEQ ID NO: 1, 2, 3, 4, 5, 6, 7, 8 or 15, in a plant cell, plant part or plant, and optionally regenerating said plant.

In an embodiment, the polynucleotide has at least 80%, more preferably at least 90%, even more preferably at least 95%, most preferably at least 98% or 99% sequence identity with the nucleic acid sequence of any of SEQ ID NO:9, 10, 11 or 13.

In an embodiment, the polypeptide comprises the amino acid sequence of any of SEQ ID NO:7 or SEQ ID NO:8, preferably SEQ ID NO:8.

The polypeptide is preferably a transcription factor protein belonging to the WRKY32 family, and may comprise two WRKY domains and may be capable of binding to at least one W-box comprised in one or more polynucleotide. The polypeptide may be a tomato WRKY32 polypeptide, and may be encoded by a Solyc07g005650 polynucleotide.

In an embodiment, the expression of said polypeptide and/or polynucleotide is impaired at least in the roots of said plant.

In an embodiment, the phenotype of the plant is not altered compared to a control plant with the exception of an improved nematode resistance.

The method may comprise the step of modifying a polynucleotide encoding a polypeptide comprising an amino acid sequence having at least 80%, more preferably at least 90%, even more preferably at least 95%, most preferably at least 98% or 99% sequence identity with the amino acid sequence of SEQ ID NO: 1, 2, 3, 4, 5, 6, 7, 8 or 15. Preferably, it comprises the step of modifying a polynucleotide encoding a polypeptide comprising an amino acid sequence having at least 80%, more preferably at least 90%, even more preferably at least 95%, most preferably at least 98% or 99% sequence identity with the amino acid sequence of SEQ ID NO:8. The modification of said polynucleotide may comprise the insertion, deletion or substitution of at least one nucleotide in said polynucleotide. The modification may, for example, be introduced using treatment with radiation or with ethyl methanesulfonate.

In an embodiment, the expression and/or activity of said polypeptide and/or polynucleotide is impaired or modified using gene silencing.

In an embodiment, said polynucleotide comprises the nucleic acid sequence of SEQ ID NO:10 or 11. Said polynucleotide may comprise the nucleic acid sequence of the Solyc07g005650 gene.

In a suitable embodiment, the plant is a tomato plant, preferably a *Solanum lycopersicum* plant.

The nematodes may be root-knot nematodes and/or cyst nematodes, and may, for instance, be selected from the genera *Meloidogyne*, *Heterodera* or *Globodera*, preferably *Meloidogyne incognita*, *Meloidogyne javanica*, *Globodera rostochiensis*, *Heterodera schachtii* and *Heterodera glycines*.

The disclosure also teaches a tomato plant, seed or cell wherein expression of a polynucleotide encoding a polypeptide comprising an amino acid sequence having at least 80%, more preferably at least 90%, even more preferably at least 95%, most preferably at least 98% or 99% sequence identity with SEQ ID NO:8 is impaired. Said polynucleotide may comprise a nucleic acid sequence that has at least 80%, more preferably at least 90%, even more preferably at least 95%, most preferably at least 98% or 99% sequence identity with the nucleic acid sequence of SEQ ID NO:10 or 11. Said polynucleotide may, for example, comprise the nucleic acid sequence of the Solyc07g005650 gene.

In an embodiment, at least one nucleotide has been inserted, deleted or substituted in said polynucleotide, preferably one or more point mutations have been introduced in said polynucleotide.

The present disclosure further teaches a tomato plant, seed or cell wherein expression and/or activity of a polypeptide comprising an amino acid sequence having at least 80%, more preferably at least 90%, even more preferably at least 95%, most preferably at least 98% or 99% sequence identity with the amino acid sequence of SEQ ID NO:8 is impaired.

In an embodiment, the polypeptide is a transcription factor protein of the WRKY32 family, comprises two WRKY domains and binds to at least one W-box comprised on one or more polynucleotides.

The tomato plant, seed or cell is preferably a *Solanum lycopersicum* plant, seed or cell.

In an embodiment, expression and/or activity of said polypeptide and/or polynucleotide is impaired in the roots, but not in the shoots. In a further embodiment, impairment of expression and/or activity does not alter the phenotype of the plant, seed or cell compared to a control plant with the exception of improved nematode resistance. In an embodiment, the tomato plant, seed or cell as taught herein exhibits improved nematode resistance, preferably improved root-knot nematode and/or cyst nematode resistance, compared to a control plant. The nematodes may be selected from the genera *Meloidogyne*, *Heterodera* or *Globodera*, preferably from the species *Meloidogyne incognita*, *Meloidogyne javanica*, and *Globodera rostochiensis*.

A rootstock of a tomato plant as taught herein is also provided, as is the use of such rootstock for improving growth and development of a graft.

The invention further provides the use of a polynucleotide encoding a polypeptide comprising an amino acid sequence having at least 80%, more preferably at least 90%, even more preferably at least 95%, most preferably at least 98% or 99% sequence identity with the amino acid sequence of SEQ ID NO:8 for improving nematode resistance in a plant cell, plant part or plant. The polypeptide is preferably a transcription factor protein of the WRKY32 family, and may comprise two WRKY domains and bind to at least one W-box comprised on one or more polynucleotides. Said polynucleotide may comprise a nucleic acid sequence that has at least 80%, more preferably at least 90%, even more preferably at least 95%, most preferably at least 98% or 99% sequence identity with the nucleic acid sequence of SEQ ID NO:10 or 11. Said polynucleotide may comprise the nucleic acid sequence of the Solyc07g005650 gene.

The invention further pertains to a method for improving nematode resistance in a plant or rootstock compared to a control plant or rootstock, comprising treating the plant or rootstock with one or more compounds that inhibit the activity of a WRKY32 protein in said plant or rootstock.

The present disclosure also teaches a method for producing a plant having improved nematode resistance compared to a control plant, comprising the step of impairing expression of a polynucleotide encoding a polypeptide comprising the amino acid sequence of SEQ ID NO:6, or a variant thereof having at least 80%, more preferably at least 90%, even more preferably at least 95%, most preferably at least 98% or 99% sequence identity to the amino acid sequence of any of SEQ ID NO:6, in a plant cell, plant part or plant, and optionally regenerating said plant, as well as a method for producing a plant having improved nematode resistance compared to a control plant, comprising the step of impairing expression and/or activity of a polypeptide comprising an amino acid sequence of SEQ ID NO:6, or a variant thereof having at least 80%, more preferably at least 90%, even more preferably at least 95%, most preferably at least 98% or 99% sequence identity to the amino acid sequence of any of SEQ ID NO:6, in a plant cell, plant part or plant, and optionally regenerating said plant.

In an embodiment, the plant or rootstock themselves or as used in any of the methods taught herein are not a transgenic plant or rootstock, and the method or use does not comprise transgenic means.

DETAILED DESCRIPTION OF THE INVENTION

Definitions

In the following description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this invention belongs. The disclosures of all publications, patent applications, patents and other references are incorporated herein in their entirety by reference.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al., Molecular Cloning. A Laboratory Manual, 2nd Edition, Cold Spring Harbor Laboratory Press, Cold Spring Harbor, N.Y., 1989; Ausubel et al., Current Protocols in Molecular Biology, John Wiley & Sons, New York, 1987 and periodic updates; and the series Methods in Enzymology, Academic Press, San Diego.

In this document and in its claims, the verb "to comprise" and its conjugations is used in its non-limiting sense to mean that items following the word are included, but items not specifically mentioned are not excluded. It encompasses the verbs "consisting essentially of" as well as "consisting of".

As used herein, the singular forms "a," "an" and "the" include plural referents unless the context clearly dictates otherwise. For example, a method for isolating "a" DNA molecule, as used above, includes isolating a plurality of molecules (e.g. 10's, 100's, 1000's, 10's of thousands, 100's of thousands, millions, or more molecules).

The term "WRKY" (pronounced as "worky") as used herein refers to a superfamily of plant transcription factors, which are key regulators of many processes in plants, including responses to biotic and abiotic stresses, immunity, plant defence, senescence, seed dormancy and seed germination, some developmental processes, and others. The WRKY transcription factor family is among the ten largest families of transcription factors in higher plants and is found throughout the green lineage (green algae and land plants). The WRKY transcription factor family comprises several members (i.e., different WRKY genes and related proteins). For instance, up to different 100 WRKY members (i.e. WRKY genes and their corresponding proteins) have been identified in *Arabidopsis* (Eulgem et al (2000), Trends in Plant Science, Vol 5, pages 199-206).

The WRKY transcription factors are characterized by the presence of at least one DNA-binding domain referred to as the "WRKY domain" (or WRKY protein domain). The WRKY domain is the most prominent features shared by all WRKY proteins, hence the name "WRKY family". The WRKY domain is characterised in that it comprises an almost invariant (i.e. highly conserved amongst family members) WRKY amino acid sequence (SEQ ID NO: 16) at the N-terminus and is about 60 residues in length. In addition, the WRKY domain also comprises an atypical zinc-finger structure at the C-terminus consisting of either Cx4-5Cx22-23HxH (SEQ ID NO: 17) (also referred to as "C2H2") or Cx7Cx23HxC (SEQ ID NO: 18) (also referred to as "C2HC"). Most WRKY transcription factors have the ability to specifically bind to a promotor element on a gene, which is referred to as "the W-box promoter element". The W-box has the consensus sequence TTGACC/T, which is the minimal consensus sequence required for specific DNA binding (Rushton et al (2010), Trends in Plant Science. Vol 15, pages 247-258).

The various WRKY family members are classified on the basis of their amino acid sequence as well as both the number of WRKY domains and the features of their zinc-finger-like motif. Based on these criteria, WRKY transcription factors have been classified into three major categories, namely group I, group II, and group III. Group I WRKY proteins (e.g. WRKT32) are characterised by the presence of two WRKY protein domains, whereas both groups II and III each possess only one WRKY protein domain. Group I and II have a C2H2 zinc finger, while group III WRKY proteins have a C2HC zinc finger instead of the C2H2 motif of group I and II factors. All three groups have been shown to specifically bind to various W-box elements on various genes (Eulgem et al (2000), Trends in Plant Science, Vol 5, pages 199-206).

The term "WRKY protein or polypeptide" or "WRKY transcription factor protein or polypeptide" as used herein refers to a protein encoded by a WRKY transcription factor gene or polynucleotide, and which comprise at least one WRKY domain capable of specifically binding to a W-box present on a gene or polynucleotide.

The term 'consensus sequence' as used herein refers to the calculated order of most frequent residues, either nucleotide or amino acid, found at each position in a sequence alignment. It represents the results of multiple sequence alignments (e.g. WRKY32 sequences) in which related sequences (e.g. WRKY32 sequences taken from different plants species belonging to the same family) are compared to each other and similar sequence motifs are calculated (e.g. using motif search program (e.g. MEME)). The skilled person is well-acquainted with the concept of 'consensus sequence' as well as with methodologies suitable for identifying consensus sequences in proteins across different plants (e.g. crop plants).

The term "Solyc07g005650 gene or polynucleotide" as used herein refers to a *Solanum lycopersicum* WRKY32 polynucleotide having the nucleic acid sequence of SEQ ID NO: 10 or 11, and which encodes the *Solanum lycopersicum* WRKY32 protein (SEQ ID NO:8) as taught herein. Orthologous genes were identified in *Arabidopsis thaliana* and other crop species.

"Expression of a gene" refers to the process wherein a DNA region, which is operably linked to appropriate regulatory regions, particularly a promoter, is transcribed into an RNA, which is biologically active, i.e. which is capable of being translated into a biologically active protein or peptide (or active peptide fragment). "Expression of a protein" is used herein interchangeably with the term expression of a gene. It refers to the process in which a DNA region, which is operably linked to appropriate regulatory regions, particularly a promoter, is transcribed into an mRNA and which is subsequently translated into a protein or peptide (or active peptide fragment). As used herein, expression of a gene or of a protein is impaired when less functional protein is produced. This may occur when transcription into an RNA is reduced and/or when the transcribed RNA is biologically inactive and/or when the transcribed RNA is translated into protein at a reduced level.

The term "gene" means a DNA sequence comprising a region (transcribed region), which is transcribed into an RNA molecule (e.g. an mRNA) in a cell, operably linked to suitable regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sequence sites.

A "chimeric gene" (or recombinant gene) refers to any gene, which is not normally found in nature in a species, in particular a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense (reverse complement of the sense strand) or inverted repeat sequence (sense and antisense, whereby the RNA transcript forms double stranded RNA upon transcription).

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked may mean that the DNA sequences being linked are contiguous.

A "transcription regulatory sequence" is herein defined as a nucleic acid sequence that is capable of regulating the rate of transcription of a (coding) sequence operably linked to the transcription regulatory sequence. A transcription regulatory sequence as herein defined will thus comprise all of the sequence elements necessary for initiation of transcription (promoter elements), for maintaining and for regulating transcription, including e.g. attenuators or enhancers. Although mostly the upstream (5') transcription regulatory sequences of a coding sequence are referred to, regulatory sequences found downstream (3') of a coding sequence are also encompassed by this definition.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. Optionally the term "promoter" includes herein also the 5' UTR region (5' Untranslated Region) (e.g. the promoter may herein include one or more parts upstream (5') of the translation initiation codon of a gene, as this region may have a role in regulating transcription and/or translation. A "constitutive" promoter is a promoter that is active in most tissues under most physiological and developmental conditions. An "inducible" promoter is a promoter that is physiologically (e.g. by external application of certain compounds) or developmentally regulated. A "tissue specific" promoter is only active in specific types of tissues or cells. A "promoter active in plants or plant cells" refers to the general capability of the promoter to drive transcription within a plant or plant cell. It does not make any implications about the spatio-temporal activity of the promoter.

A "3' UTR" or "3' non-translated sequence" (also often referred to as 3' untranslated region, or 3'end) refers to the nucleic acid sequence found downstream of the coding sequence of a gene, which comprises for example a transcription termination site and (in most, but not all eukaryotic mRNAs) a polyadenylation signal (such as e.g. AAUAAA or variants thereof). After termination of transcription, the mRNA transcript may be cleaved downstream of the polyadenylation signal and a poly(A) tail may be added, which is involved in the transport of the mRNA to the cytoplasm (where translation takes place).

The term "cDNA" means complementary DNA. Complementary DNA is made by reverse transcribing RNA into a complementary DNA sequence. cDNA sequences thus correspond to RNA sequences that are expressed from genes. As mRNA sequences when expressed from the genome can undergo splicing, i.e. introns are spliced out of the mRNA and exons are joined together, before being translated in the cytoplasm into proteins, it is understood that expression of a cDNA means expression of the mRNA that encodes for the cDNA. The cDNA sequence thus may not be identical to the genomic DNA sequence to which it corresponds as cDNA may encode only the complete open reading frame, consisting of the joined exons, for a protein, whereas the genomic DNA encodes and exons interspersed by intron sequences. Genetically modifying a gene which encodes the cDNA may thus not only relate to modifying the sequences corresponding to the cDNA, but may also involve mutating intronic sequences of the genomic DNA and/or other gene regulatory sequences of that gene, as long as it results in the impairment of gene expression.

A nucleic acid molecule or polynucleotide according to the present invention may include any polymer or oligomer of pyrimidine and purine bases, preferably cytosine, thymine, and uracil, and adenine and guanine, respectively (See Albert L. Lehninger, Principles of Biochemistry, at 793-800 (Worth Pub. 1982) which is herein incorporated by reference in its entirety for all purposes). The present invention contemplates any deoxyribonucleotide, ribonucleotide or peptide nucleic acid component, and any chemical variants thereof, such as methylated, hydroxymethylated or glycosylated forms of these bases, and the like. The polymers or oligomers may be heterogeneous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

Targeted nucleotide exchange (TNE) is a process by which a synthetic oligonucleotide, partially complementary to a site in a chromosomal or an episomal gene directs the reversal of a single nucleotide at a specific site. TNE has been described using a wide variety of oligonucleotides and targets. Some of the reported oligonucleotides are RNA/DNA chimeras, contain terminal modifications to impart nuclease resistance.

With the term "aligning" and "alignment" is meant the comparison of two or more nucleotide sequences based on the presence of short or long stretches of identical or similar nucleotides. Several methods for alignment of nucleotide sequences are known in the art, as will be further explained below.

"Sequence identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER; Gribskov, M. and Devereux, J., eds., M Stockton Press, New York, 1991). While a number of methods exist to measure identity between two polynucleotide or polypeptide sequences, the term "identity" is well known to skilled artisans (Carillo, H., and Lipton, D., SIAM J. Applied Math (1988) 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., SIAM J. Applied Math (1988) 48:1073. Methods to determine identity and similarity are codified in computer programs. Preferred computer program methods to determine identity and similarity between two sequences include, but are not limited to, GCS program package (Devereux, J., et al., Nucleic Acids Research (1984) 12(1):387), BLASTP, BLASTN, FASTA (Atschul, S. F. et al., J. Molec. Biol. (1990) 215:403).

As an illustration, by a polynucleotide having a nucleotide sequence having at least, for example, 95% "identity" to a reference nucleotide sequence encoding a polypeptide of a certain sequence it is intended that the nucleotide sequence of the polynucleotide is identical to the reference sequence except that the polynucleotide sequence may include up to five point mutations per each 100 nucleotides of the reference polypeptide sequence. Hence, the percentage of identity of a nucleotide sequence to a reference nucleic acid sequence is calculated over the entire length of the reference nucleic acid sequence. In other words, to obtain a polynucleotide having a nucleotide sequence at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence. These mutations of the reference sequence may occur at the 5' or 3' terminal positions of the reference nucleotide sequence, or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence is intended that the amino acid sequence of the polypeptide is identical to the reference sequence except that the polypeptide sequence may include up to five amino acid alterations per each 100 amino acids of the reference amino acid sequence. Hence, the percentage of identity of an amino acid sequence to a reference amino acid sequence is calculated over the entire length of the reference amino acid sequence. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy-terminal positions of the reference amino acid sequence or anywhere between those terminal positions, interspersed either individually among residues in the reference sequence or in one or more contiguous groups within the reference sequence.

The terms "protein" or "polypeptide" are used interchangeably and refer to molecules consisting of a chain of amino acids, without reference to a specific mode of action, size, 3 dimensional structure or origin. A "fragment" or "portion" of a protein may thus still be referred to as a "protein". An "isolated protein" is used to refer to a protein which is no longer in its natural environment, for example in vitro or in a recombinant bacterial or plant host cell.

The term "transgenic plant" as used herein refers to a plant, plant cell, callus, plant tissue, or plant part whose genetic material has been altered using genetic modification (e.g., transfection or transformation with a gene vector construct to introduce a new gene or polynucleotide in the plant). Genetic modification is a process in which exogenous DNA fragments from outside the cell or organism are integrated in the genome of living cells. This integration may be stable. The exogenous DNA fragments may for instance be larger than 20, 50, 100, 500, 1000, 5000 or 10000 base pairs. Genetic modification includes recombinant nucleic acid (DNA or RNA) techniques. It includes transfer of genes or parts of genes across species boundaries and the creation of transgenic cells and organisms. As a consequence of genetic modification, the plant possesses a novel combination of genetic material, e.g., a foreign gene or polynucleotide from an unrelated organism has been added to the plant genome or a recombinant polynucleotide has been stably integrated into a chromosome or stable extra-chromosomal element, so that it is passed on to successive generations.

The term "non-transgenic plant" as used herein refers to a plant whose genetic makeup has not been altered or has been altered without the addition of genetic material from an unrelated organism. The term "non-transgenic pant" also encompasses plants which have been subjected to genome editing, e.g., using targeted nucleotide exchange (TNE) technology.

"Genome editing" is a process in which genomic DNA of a living cell is altered by inserting, replacing, or removing one or more bases using mutagenic molecules. The number of bases inserted, replaced or removed may for instance be 1, 2, 5, 10, 15, 20, 25, 30, 50 or more. The mutagenic molecules used can, for instance, be gene repair oligonucleotides or endonucleases artificially engineered to create specific double-strand breaks (DSBs) or single-strand nicks at predefined locations in the genome. The breaks or nicks are repaired by the cell's own repair mechanisms using natural processes of mismatch repair, base excision repair, homologous recombination or non-homologous end-joining (NHEJ). There are currently four families of engineered nucleases being used: Zinc finger nucleases (ZFNs), Transcription Activator-Like Effector Nucleases (TALENs), the CRISPR/Cas9 system, and engineered homing endonucleases or meganucleases. Genome editing can also be achieved by oligonucleotide-directed mutagenesis using oligonucleotides (ODM), also referred to as targeted nucleotide exchange (TNE). Genome editing includes site-specific mutagenesis, site-specific gene addition and gene targeting. Genome editing does not encompass the stable introduction of exogenous DNA.

The term "endogenous" as used in the context of the present invention in combination with protein or gene (e.g. WRKY32) means that said protein or gene (WRKY32) originates from the plant in which it is still contained. Often an endogenous gene will be present in its normal genetic context in the plant. In the present invention, an endogenous protein or gene (e.g. WRKY32) may be modified in situ (in the plant or plant cell) using standard molecular biology methods, e.g. gene silencing, TNE and others.

"Plant" refers to either the whole plant or to parts of a plant, such as cells, tissue or organs (e.g. pollen, seeds, gametes, roots, leaves, flowers, flower buds, anthers, fruit, etc.) obtainable from the plant, as well as derivatives of any of these and progeny derived from such a plant by selfing or crossing. "Plant cell(s)" include protoplasts, gametes, suspension cultures, microspores, pollen grains, etc., either in isolation or within a tissue, organ or organism.

The term "rootstock" as used herein refers to part of a plant, often an underground part, from which new aboveground growth can be produced. For instance, it may refer to a rhizome or underground stem. In grafting, it refers to a plant, sometimes just a stump, which already has an established, healthy root system, onto which a cutting or a bud from another plant is grafted.

A "control plant" as referred to herein is a plant of the same species and preferably same genetic background as the plant having been subjected to the methods as taught herein and as a result have improved or increased nematode resistance. The control plant preferably comprises the endogenous, functional WRKY32 gene and expresses said gene and corresponding WRKY32 protein, and is preferably a wild type plant. The control plant is susceptible to nematode infection or develop symptoms of nematode infection or has low resistance to nematode infection, e.g., nematodes (root-knot or cyst nematodes) can successfully invade, establish themselves and develop in the control plant.

"Nematode resistance" refers herein to various levels of nematode resistance or tolerance of a plant, including moderate resistance and high resistance or complete resistance to one or more nematodes (e.g. root-knot or cyst nematodes). It can be measured and optionally quantified by comparison of disease caused symptoms (such as frequency and/or size of hypersensitive response (HR) lesions, etc.) relative to those seen in susceptible control plants when grown under identical disease pressure. Such disease bioassays can be carried out using known methods. Nematode resistance can also be indirectly measured as higher yield of resistant plants compared to susceptible plants when grown under disease pressure.

"Nematode caused symptoms" include any symptoms of disease, such as feeding sites, galls, retarded growth, plus opportunity of secondary infection of other pathogens, withdrawal of nutrients, etc.

"Improved nematode resistance" refers to an increase in nematode resistance of a plant or plant tissue compared to a suitable control plant. Both a qualitative increase (e.g. from susceptible to resistant) and a quantitative increase are encompassed herein. Also encompassed is both a reduction of disease incidence (percentage of plants becoming infected) and/or of disease severity. Preferably, a plant having improved nematode resistance to at least one nematode (e.g. root-knot and/or cyst nematode) is a plant comprising at least 1%, 2%, 5%, 10%, 15%, 20%, 30%, 50%, 70%, 80%, 90%, or even 100% higher levels of resistance to said nematode than the control plant, using suitable bioassays and/or field assays for assessing disease resistance. For example, the number of root knots developed in response to nematode infection may be determined in both a plant as taught herein and a control plant, and may be compared, as shown in the Examples section.

Method for Producing a Plant Having Improved Nematode Resistance

The present inventors have identified a plant gene, which belongs to the WRKY super family, more specifically a WRKY32 gene, that is significantly suppressed or down-regulated in giant cells upon infection by *Meloidogyne* nematode species (e.g. root-knot or cyst nematodes), but unchanged in infected root tissues larger than the giant cells (e.g. galls or infected root segments). It was surprisingly found that when the expression of this gene (WRKY32 gene) was altered or impaired, in casu by gene silencing, resulting in impaired expression of functional WRKY32 protein, a decrease in disease symptoms caused by root-knot or cyst nematodes was observed in said plant. For instance, it was surprisingly found that knocking-down of the expression of the WRKY32 gene (e.g. tomato homologous sequence (Solyc07g005650) in a crop plant (tomato plant), using RNAi-based transformation, caused a decreased in the number of infections and/or decreased the severity of infection typically caused by root-knot or cyst nematodes in said crop plant.

In a first aspect, the present invention relates to a method for producing a plant having improved nematode resistance compared to a control plant, comprising the step of impairing the expression and/or the activity of an endogenous WRKY32 polypeptide or impairing the expression of a WRKY32 polynucleotide in said plant.

In an embodiment, the expression and/or activity of any WRKY32 polypeptides or the expression of any WRKY32 polynucleotides may be impaired in any plant comprising said WRKY32 polypeptides and/or WRKY32 polynucleotides so as to confer improved or increased nematode resistance to said plant.

The term "WRKY32 polypeptide or protein" as used herein refers to a polypeptide that is a family member of the WRKY polypeptide superfamily. WRKY32 protein is encoded by a WRKY32 gene or polynucleotide that is a family member of the WRKY polynucleotide superfamily. The WRKY32 polypeptide belongs to group I WRKY polypeptide or protein. The WRKY32 polypeptides comprise two WRKY domains capable of specifically binding to one or more W-box(es) comprised on one or more genes, and further comprise a zinc finger having a C2H2 motif. Non-limiting examples of WRKY32 proteins or polypeptides include the Solanaceae consensus WRKY32 protein (comprising the amino acid sequence of SEQ ID NO:1), Brassicaceae consensus WRKY32 protein sequence (SEQ ID NO:2), Cucurbitaceae consensus WRKY32 protein (comprising the amino acid sequence of SEQ ID NO:3), Fabaceae consensus WRKY32 protein (comprising the amino acid sequence of SEQ ID NO:4), Rosaceae consensus WRKY32 protein (comprising the amino acid sequence of SEQ ID NO:5), Poaceae consensus WRKY32 protein (comprising the amino acid sequence of SEQ ID NO:6), *Solanum* consensus WRKY32 protein (comprising the amino acid sequence of SEQ ID NO:7), and the *Solanum lycopersicum* WRKY32 protein (comprising the amino acid sequence of SEQ ID NO:8), and the *Arabidopsis thaliana* WRKY32 protein (comprising the amino acid sequence of SEQ ID NO:15).

The term "Solanaceae consensus WRKY32 protein sequence" as used herein refers to a specific WRKY32 protein sequence that is highly conserved among all Solanaceae species, and which has the amino acid sequence of SEQ ID NO:1. In an embodiment, the Solanaceae consensus WRKY32 protein sequence (SEQ ID NO:1) and variants thereof may be used (e.g. by modifying its expression and/or activity in a plant) to improve nematode resistance in a plant, preferably a plant species belonging to the Solanaceae family.

The term "Brassicaceae consensus WRKY32 protein sequence" as used herein refers to a specific WRKY32 protein sequence that is highly conserved among all Brassicaceae species, and which has the amino acid sequence of SEQ ID NO:2. In an embodiment, the Brassicaceae consensus WRKY32 protein sequence (SEQ ID NO:2) and variants thereof may be used (e.g. by modifying its expression and/or activity in a plant) to improve nematode resistance in a plant, preferably a plant species belonging to the Brassicaceae family.

The term "Cucurbitaceae consensus WRKY32 protein sequence" as used herein refers to a specific WRKY32 protein sequence that is highly conserved among all Cucurbitaceae species, and which has the amino acid sequence of SEQ ID NO:3. In an embodiment, the Cucurbitaceae consensus WRKY32 protein sequence (SEQ ID NO:3) and variants thereof may be used (e.g. by modifying its expression and/or activity in a plant) to improve nematode resistance in a plant, preferably a plant species belonging to the Cucurbitaceae family.

The term "Fabaceae consensus WRKY32 protein sequence" as used herein refers to a specific WRKY32 protein sequence that is highly conserved among all Fabaceae species, and which has the amino acid sequence of SEQ ID NO:4. In an embodiment, the Fabaceae consensus WRKY32 protein sequence (SEQ ID NO:4) and variants thereof may be used (e.g. by modifying its expression and/or activity in a plant) to improve nematode resistance in a plant, preferably a plant species belonging to the Fabaceae family.

The term "Rosaceae consensus WRKY32 protein sequence" as used herein refers to a specific WRKY32 protein sequence that is highly conserved among all Rosaceae species, and which has the amino acid sequence of SEQ ID NO:5. In an embodiment, the Rosaceae consensus WRKY32 protein sequence (SEQ ID NO:5) and variants thereof may be used (e.g. by modifying its expression and/or activity in a plant) to improve nematode resistance in a plant, preferably a plant species belonging to the Rosaceae family.

The term "Poaceae consensus WRKY32 protein sequence" as used herein refers to a specific WRKY32 protein sequence that is highly conserved among all Poaceae species, and which has the amino acid sequence of SEQ ID NO:6. In an embodiment, the Poaceae consensus WRKY32 protein sequence (SEQ ID NO:6) and variants thereof may be used (e.g. by modifying its expression and/or activity in a plant) to improve nematode resistance in a plant, preferably a plant species belonging to the Poaceae family.

The term "*Solanum* consensus WRKY32 protein sequence" as used herein refers to a specific WRKY32 protein sequence that is highly conserved among all *Solanum* species, and which has the amino acid sequence of SEQ ID NO:7. In an embodiment, the *Solanum* consensus WRKY32 protein sequence (SEQ ID NO:7) and variants thereof may be used (e.g. by modifying its expression and/or activity in a plant) to improve nematode resistance in a plant, preferably a plant species belonging to the *Solanum* genus (e.g. *Solanum lycopersicum*).

The term "*Solanum* consensus coding (cDNA) WRKY32 nucleic acid sequence" as used herein refers to a specific WRKY32 nucleic acid sequences that is highly conserved among all *Solanum* species, and which have the nucleic acid sequence of SEQ ID NO: 9, and which encodes the *Solanum* consensus WRKY32 protein sequence (SEQ ID NO:7) as taught herein. In an embodiment, the *Solanum* consensus coding (cDNA) WRKY32 nucleic acid sequence (SEQ ID NO:9) and variants thereof may be used (e.g. by modifying its expression in a plant) to improve nematode resistance in a plant, preferably a plant species belonging to the *Solanum* genus (e.g. *Solanum lycopersicum*).

In a further aspect, the present invention relates to a method for producing a plant having improved or increased nematode resistance compared to a control plant, comprising the step of impairing expression and/or activity of a polypeptide comprising an amino acid sequence of any of SEQ ID NO: 1, 2, 3, 4, 5, 6, 7, 8 or 15, or a variant thereof having at least 80%, more preferably at least 90%, even more preferably at least 95%, most preferably at least 98% or 99% sequence identity to the amino acid sequence of any of SEQ ID NO: 1, 2, 3, 4, 5, 6, 7, 8 or 15, in a plant cell, plant part or plant, and optionally regenerating said plant.

In yet a further aspect, the present invention relates to a method for producing a plant having improved nematode resistance compared to a control plant, comprising the step of impairing the expression of a polynucleotide encoding a polypeptide comprising the amino acid sequence of any of SEQ ID NO:1, 2, 3, 4, 5, 6, 7, 8 or 15, or a variant thereof having at least 80%, more preferably at least 90%, even more preferably at least 95%, most preferably at least 98% or 99% sequence identity to the amino acid sequence of any of SEQ ID NO: 1, 2, 3, 4, 5, 6, 7, 8 or 15, in a plant cell, plant part or plant, and optionally regenerating said plant.

In a preferred embodiment, the polynucleotide as taught herein may have at least 80%, more preferably at least 90%, even more preferably at least 95%, most preferably at least 98% or 99% sequence identity with the nucleic acid sequence of any of SEQ ID NO:9, 10, 11, 13 or 14.

The term "impairing the expression of a polynucleotide (gene) or polypeptide (protein)" as used herein, refers to a situation where the level of protein (e.g. WRKY32) or RNA (e.g. WRKY32 mRNA) produced in a modified plant or plant cell is reduced compared to the level of protein or gene produced in a suitable control plant or plant cell (e.g., a wild type plant or plant cell). Preferably, expression of a gene or protein (e.g. WRKY32) is impaired when the level of gene or protein (e.g. WRKY32) produced in a plant or plant cell is at least 1%, 2%, 5%, 10%, 15%, 20%, 30%, 50%, 70%, 80%, 90%, or even 100% lower than the level of gene or protein (e.g. WRKY32 protein) that is produced in the control plant. Alternatively, expression of a gene or protein is impaired when the level of gene or protein produced in a plant or plant cell is statistically significantly lower than the level of gene or protein that is produced in the control plant. "Impairing expression of a polynucleotide or polypeptide" according to the present invention denotes the absence or reduced presence of a functional WRKY32 gene (i.e. mRNA) or protein or variants thereof. This may for instance result in preventing or disrupting the expression of one or more downstream genes and/or proteins that are under the control of WRKY32 protein or regulated by WRKY32 protein, causing a change in the plant physiology (e.g. increase resistance to nematode). The skilled person will readily be capable of establishing whether or not expression of a gene or protein (e.g. WRKY32) is impaired.

The term "impairing the activity of a protein" (e.g. WRKY32 protein) as used herein refers to a situation where the natural activity of a protein, such as for example its ability to bind to a promoter element, to bind to a receptor, to catalyse an enzymatic reaction, to regulate gene expression, etc, is altered or reduced or blocked or inhibited compared to the activity of the same protein in a control plant. Preferably, the activity of a protein (e.g. WRKY32) may be considered to be impaired when the activity of a protein (e.g. WRKY32 protein) produced in a plant or plant cell is at least 1%, 2%, 5%, 10%, 15%, 20%, 30%, 50%, 70%, 80%, 90%, or even 100% lower than the activity of the same protein (e.g. WRKY32 protein) produced in a control plant. "Impairing the activity of a protein or polypeptide" according to the present invention denotes the absence or reduced activity of a functional WRKY32 protein and variants thereof, where for instance, the WRKY32 protein or a variant thereof cannot bind or bind with less affinity or efficacy to a W-box on a gene or cannot regulate or regulate to a lesser extent the expression of the gene(s) under its control or influence. This may for instance prevent or disrupt the expression of one or more downstream genes and/or proteins that are under the control of WRKY32 protein or regulated by WRKY32 protein, causing a change in the plant physiology (e.g. increase or improved resistance to nematode). The skilled person will readily be capable of establishing whether or not activity of a protein (e.g. WRKY32) is impaired, e.g. by assessing the ability of the WRKY32 proteins or variants thereof to bind to a W-box or by assessing the downstream effects of impaired WRKY32 protein activity on the expression pattern of the genes regulated by WRKY32 proteins or variants thereof. In the present invention, an impaired or modified WRKY32 protein exhibits impaired activity compared to an endogenous WRKY32 protein when its activity is significantly lower than the endogenous WRKY32 protein from which it is derived. For example, said impaired or modified WRKY32 protein exhibits impaired activity compared to an endogenous WRKY32 protein, preferably an endogenous WRKY32 protein from which it is derived, when its specific activity is at least 1%, 2%, 5%, 10%, 15%, 20%, 30%, 50%, 70%, 80%, 90%, or even 100% lower than the specific activity of the endogenous WRKY32 protein from which it is derived.

The term "dysfunctional" or "less functional" in relation to WRKY32 proteins or variants thereof, such as orthologues or mutants, and fragments, as used herein refers to the capability to increase or improve the (quantitative and/or qualitative) nematode resistance, e.g., by impairing (e.g. by silencing) the expression level of the gene(s) in a plant susceptible to nematode (e.g. root-knot or cyst nematode) infection. The functionality of a WRKY32 protein and variants thereof obtained from plant species X can be tested by various methods. Preferably, silencing of or knocking out the gene encoding the WRKY32 protein in plant species X, using e.g. gene silencing vectors, will lead to an improved nematode resistance as can be tested as explained herein in detail. Also, complementation of a knockout of the gene with a functional WRKY32 protein in a plant will restore or confer sensitivity to nematode infection, i.e. sensitivity to nematode infection will be restored in said plant. The skilled person will have no difficulties in testing functionality of WRKY32 and variants thereof. Expression of "dysfunctional" or "impaired" WRKY32 protein in a plant in the absence of any functional or non-impaired WRKY32 protein will confer improved nematode resistance to said plant, i.e. plant will not develop symptoms of nematode infection or will be affected to a lesser degree (e.g. minor manifestation of nematode infection) as compared to a control plant comprising an endogenous WRKY32 protein.

The invention further pertains to a method for producing a plant having improved or increased nematode resistance compared to a control plant comprising the step of modifying a polynucleotide encoding a polypeptide comprising the amino acid sequence of any of SEQ ID NO:1, 2, 3, 4, 5, 6, 7, 8 or 15, or a variant thereof having at least 80%, preferably at least 85%, more preferably at least 90%, even more preferably at least 95%, most preferably at least 98% or 99% sequence identity to the amino acid sequence of any of SEQ ID NO: 1, 2, 3, 4, 5, 7, 8 or 15, e.g., a WRKY32 gene, in a plant cell, plant part or plant to obtain a modified polynucleotide encoding a modified polypeptide, which modified polypeptide exhibits impaired activity compared to the polypeptide comprising the amino acid sequence of any of SEQ ID NO:1, 2, 3, 4, 5, 6, 7, 8 or 15, or a variant thereof having at least 80%, preferably at least 85%, more preferably at least 90%, even more preferably at least 95%, most preferably at least 98% or 99% sequence identity to the amino acid sequence of any of SEQ ID NO: 1, 2, 3, 4, 5, 6, 7, 8 or 15.

In an embodiment, the polypeptide may comprise the amino acid sequence of any of SEQ ID NO:7 or 8, or a variant thereof having at least 80%, preferably at least 85%, more preferably at least 90%, even more preferably at least 95%, most preferably at least 98% or 99% sequence identity to the amino acid sequence of any of SEQ ID NO: 7 or 8.

In a preferred embodiment, the polypeptide as taught herein may comprise the amino acid sequence of any of SEQ ID NO:8 or a variant thereof having at least 80%, preferably at least 85%, more preferably at least 90%, even more preferably at least 95%, most preferably at least 98% or 99% sequence identity to the amino acid sequence of any of SEQ ID NO: 8.

In an embodiment, the polypeptide as taught herein is a transcription factor protein belonging to the WRKY32 family. Thus said polypeptide has the characteristics of Group I WRKY32 proteins as taught herein, i.e. two WRKY domains capable of specifically binding to one or more W-box(es) comprised on one or more gene(s) or polynucleotides and further comprises a zinc finger having a C2H2 motif.

Therefore, in a preferred embodiment, the WRKY32 polypeptide as taught herein comprises two WRKY domain and is capable of binding to at least one W-box comprised in a polynucleotide.

In a preferred embodiment, the polypeptide as taught herein is a tomato WRKY32 polypeptide, preferably said polypeptide is encoded by a Solyc07g005650 polynucleotide or gene, which has the nucleic acid sequence of SEQ ID NO: 10 or 11.

In an embodiment, the expression and/or activity of the polypeptides and/or the expression of the polynucleotides as taught herein is impaired at least in the roots of said plant, which represents a main area typically infected by nematodes (e.g. root-knot or cyst nematodes), and where symptoms (e.g. galls or root knots) of nematode infection are typically visible or prominent.

In an embodiment, the phenotype of the plant as taught herein is not altered compared to a control plant, with the exception of said plant having an improved nematode resistance compared to said control plant. For instance, yield, reproduction, flowering, growth, development, etc. is not affected in plants subjected to the methods according to the invention compared to a control plant or wild type plant, preferably of the same species.

Thus in an embodiment, the methods as taught herein may comprise the step of modifying an endogenous polynucleotide encoding a polypeptide comprising an amino acid sequence having at least 80%, more preferably at least 90%, even more preferably at least 95%, most preferably at least 98% or 99% sequence identity with the amino acid sequence of SEQ ID NO: 1, 2, 3, 4, 5, 6, 7, 8 or 15.

In a preferred embodiment, the methods as taught herein may comprise the step of modifying a polynucleotide encoding a polypeptide comprising an amino acid sequence having at least 80%, more preferably at least 90%, even more preferably at least 95%, most preferably at least 98% or 99% sequence identity with the amino acid sequence of SEQ ID NO:8.

For instance in an embodiment, this may be achieved by impairing or modifying a polynucleotide comprising the nucleic acid sequence of SEQ ID NO:10 or 11 or the nucleic acid sequence of the Solyc07g005650 gene.

In the methods as taught herein, it is understood that impairing the expression and/or the activity of an endogenous WRKY32 polypeptide or impairing the expression of a WRKY32 polynucleotide as taught herein in a plant may be achieved by any suitable means. For instance, it may be achieved by modifying an endogenous WRKY32 polynucleotide to encode a modified WRKY32 polypeptide that is less functional or lacks WRKY32 function or activity compared to the endogenous WRKY32 polypeptide in said plant. For instance, a WRKY32 polypeptide that lacks function or activity may be a WRKY32 polypeptide that cannot bind to or bind with less affinity or efficiency to a W-box present on a gene or polynucleotide or fail to regulate or influence the expression of the gene(s) downstream or under the control of said functionally impaired WRKY32 polypeptide, despite binding to the W-box comprised on a gene, thus globally impeding invasion by nematodes (i.e. improving or increasing nematode resistance).

For instance, in an embodiment, impairing or modifying the polypeptides or polynucleotides as taught may be performed by using treatment with radiation or with ethyl methanesulfonate. In a further embodiment, impairing or modifying the polypeptides or polynucleotides as taught may be performed by mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such modified plants. Seeds may for example be radiated or chemically treated and the plants screened for a modified phenotype, such as improved nematode resistance and/or HR lesions.

In yet a further embodiment, the expression of said polypeptide and/or polynucleotide may be impaired using gene silencing methods, which include RNAi and VIGS.

In an embodiment, impairing or modifying the polypeptides or polynucleotides as taught may be performed by using targeted mutagenesis methods include, without limitation, those employing zinc finger nucleases, Cas9-like, Cas9/crRNA/tracrRNA or Cas9/gRNA CRISPR systems, or targeted mutagenesis methods employing mutagenic oligonucleotides, possibly containing chemically modified nucleotides for enhancing mutagenesis with sequence complementarity to the WRKY32 gene, into plant protoplasts (e.g., KeyBase® or TALENs).

Alternatively, mutagenesis systems such as TILLING (Targeting Induced Local Lesions IN Genomics; McCallum et al., 2000, Nat Biotech 18:455, and McCallum et al. 2000, Plant Physiol. 123, 439-442, both incorporated herein by reference) may be used to generate plant lines which provide an WRKY32 gene encoding a WRKY32 protein having one or more of the above mutations and/or having enhanced disease resistance to one or more nematodes. TILLING uses traditional chemical mutagenesis (e.g. EMS mutagenesis) followed by high-throughput screening for mutations. Thus, plants, seeds and tissues comprising an WRKY32 gene having one or more of the desired mutations may be obtained.

In an embodiment, impairing or modifying a polynucleotide and/or polypeptide as taught herein may include the insertion, deletion or substitution of at least one nucleotide in said polynucleotide.

It is understood that any of the means used to impair the expression and/or activity of an endogenous WRKY32 polypeptide or variants thereof or to impair the expression of an endogenous WRKY32 polynucleotide or variants thereof as taught herein are capable of causing a functional mutation (e.g. deletion or insertion or substitution of a nucleotide or amino acid or point mutation, which disrupts or alters protein or gene function, e.g. by introducing a nonsense mutation to create a premature stop codon) or causing a loss of function (knock out of the natural function, e.g. by gene silencing). The skilled person is well acquainted with methods to introduce functional mutations in a nucleic acid sequence or amino acid sequence so as to alter or block or inhibit the function of the resulting polynucleotide or polypeptide.

In an embodiment, the plant as taught herein may be any plant. Non-limiting examples of suitable plant includes any plants species belonging to the Solanaceae family, Brassicaceae family, Cucurbitaceae family, Fabaceae family, Rosaceae family, Poaceae family, or *Solanum* genus.

In a preferred embodiment, the plant as taught herein may be any plant species from the *Solanum* genus. In a further preferred embodiment, the plant as taught herein may be a tomato plant, more preferably a *Solanum lycopersicum* plant. It was surprisingly found that it was sufficient to impair (e.g. using RNAi gene silencing technology) the expression and/or activity of the endogenous *Solanum lycopersicum* WRKY32 protein (i.e. SEQ ID NO:8) or the expression of the endogenous *Solanum lycopersicum* WRKY32 gene (SEQ: ID NO:10 or 11 or Solyc07g005650 gene) in said *Solanum lycopersicum* tomato plant to make or render said plant significantly more resistant (less symptoms of nematode infection) to nematode (e.g. root-knot nematode) infection compared to control plants.

In an embodiment, the methods of the present invention further comprise the step of screening the regenerated plant, or a plant derived therefrom by selfing or crossing, for improved resistance to one or more nematodes and identifying a plant comprising improved or increased resistance to one or more of said nematodes.

In a further aspect, the present invention relates to a method for improving nematode resistance in a plant or rootstock compared to a control plant or rootstock, comprising treating the plant or rootstock with one or more compounds that inhibit the activity of a WRKY32 protein in said plant or rootstock.

The invention also relates to a method for producing a plant having improved nematode resistance compared to a control plant, comprising the step of impairing expression of a polynucleotide encoding a polypeptide comprising the amino acid sequence of SEQ ID NO:6, or a variant thereof having at least 80%, more preferably at least 90%, even more preferably at least 95%, most preferably at least 98% or 99% sequence identity to the amino acid sequence of any of SEQ ID NO:6, in a plant cell, plant part or plant, and optionally regenerating said plant, or comprising the step of impairing expression of a polypeptide comprising an amino acid sequence of SEQ ID NO:6, or a variant thereof having at least 80%, more preferably at least 90%, even more preferably at least 95%, most preferably at least 98% or 99% sequence identity to the amino acid sequence of any of SEQ ID NO:6, in a plant cell, plant part or plant, and optionally regenerating said plant.

Plants

In a further aspect, the present invention also relates to a plant, plant part, plant cell, seed, and/or rootstock obtainable by any one of the methods above.

In an embodiment, the present invention pertains to a plant, plant part, plant cell, seeds, and/or rootstock comprising an impaired or modified WRKY32 polynucleotide and/or WRKY32 polypeptide as taught herein.

In an embodiment, the present invention further pertains to a plant, plant part, plant cell, seeds and/or rootstock, in which expression of an endogenous WRKY32 polynucleotide and/or an endogenous WRKY32 polypeptide is modified as taught herein.

Said plant, plant part, plant cell, seed, and/or rootstock may be any plant, plant part, plant cell, seed, and/or rootstock, in which expression of an endogenous WRKY32 polynucleotide is knocked out, e.g., by means of a T-DNA insertion, or a plant, plant part, plant cell, seed, and/or rootstock may be any plant, plant part, plant cell, seed, and/or rootstock in which expression of an endogenous WRKY32 gene is silenced, e.g., using RNAi.

In an embodiment, said plant, plant part, plant cell, seed, and/or rootstock may be from any plant species belonging to the Solanaceae family, Brassicaceae family, Cucurbitaceae family, Fabaceae family, Rosaceae family, Poaceae family, or *Solanum* genus.

Preferably, the plant as taught herein is a crop plant or a cultivated plant, i.e. plant species which is cultivated and bred by humans. A crop plant may be cultivated for food or feed purposes (e.g. field crops), or for ornamental purposes (e.g. production of flowers for cutting, grasses for lawns, etc.). A crop plant as defined herein also includes plants from which non-food products are harvested, such as oil for fuel, plastic polymers, pharmaceutical products, cork, fibres (such as cotton) and the like. Preferably, the plant part, plant cell, seed, and/or rootstock as taught herein are from a crop plant.

In an embodiment, the plant, plant part, plant cell, seed, and/or rootstock may be a monocotyledonous plant or a dicotyledonous plant, plant part, plant cell, seed, and/or rootstock. For example, the plant, plant part, plant cell, seed, and/or rootstock may belong to the genus *Solanum* (including *Lycopersicum*), *Nicotiana, Capsicum, Petunia* and other genera. The following plant species may suitably be used: tobacco (*Nicotiana* species, e.g. *N. benthamiana, N. plumbaginifolia, N. tabacum,* etc.), vegetable species, such as tomato (*Solanum lycopersicum*) such as e.g. cherry tomato, var. *cerasiforme* or currant tomato, var. *pimpinellifolium*) or tree tomato (*S. betaceum,* syn. *Cyphomandra betaceae*), potato (*Solanum tuberosum*), eggplant (*Solanum melongena*), pepi no (*Solanum muricatum*), cocona (*Solanum sessiliflorum*) and naranjilla (*Solanum quitoense*), peppers (*Capsicum annuum, Capsicum frutescens, Capsicum baccatum*), ornamental species (e.g. *Petunia hybrida, Petunia axillaries, P. integrifolia*), coffee (*Coffea*).

In an embodiment, the plant, plant part, plant cell, seed, and/or rootstock as taught herein may belong to any other family, such as to the Cucurbitaceae or Gramineae. Suitable host plants include for example maize/corn (*Zea* species), wheat (*Triticum* species), barley (e.g. *Hordeum vulgare*), oat (e.g. *Avena sativa*), sorghum (*Sorghum bicolor*), rye (*Secale cereale*), soybean (Glycine spp, e.g. *G. max*), cotton (*Gossypium* species, e.g. *G. hirsutum, G. barbadense*), *Brassica* spp. (e.g. *B. napus, B. juncea, B. oleracea, B. rapa,* etc), sunflower (*Helianthus annus*), safflower, yam, cassava, alfalfa (*Medicago sativa*), rice (*Oryza* species, e.g. *O. sativa* indica cultivar-group or *japonica* cultivar-group), forage grasses, pearl millet (*Pennisetum* spp. e.g. *P. glaucum*), tree species (*Pinus,* poplar, fir, plantain, etc), tea, *coffea,* oil palm, coconut, vegetable species, such as pea, zucchini, beans (e.g. *Phaseolus* species), cucumber, artichoke, asparagus, broccoli, garlic, leek, lettuce, onion, radish, turnip, Brussels sprouts, carrot, cauliflower, chicory, celery, spinach, endive, fennel, beet, fleshy fruit bearing plants (grapes, peaches, plums, strawberry, mango, apple, plum, cherry, apricot, banana, blackberry, blueberry, citrus, kiwi, figs, lemon, lime, nectarines, raspberry, watermelon, orange, grapefruit, etc.), ornamental species (e.g. Rose, *Petunia, Chrysanthemum, Lily, Gerbera* species), herbs (mint, parsley, basil, thyme, etc.), woody trees (e.g. species of *Populus, Salix, Quercus, Eucalyptus*), fibre species e.g. flax (*Linum usitatissimum*) and hemp (*Cannabis sativa*).

In an embodiment, said plant, plant part, plant cell, seed, and/or rootstock is not an *Arabidopsis thaliana* plant, plant part, plant cell, seed, and/or rootstock comprising a T-DNA insertion in AT5G24910. In another embodiment, said plant, plant part, plant cell, seed, and/or rootstock is not an *Arabidopsis thaliana* plant, plant part, plant cell, seed, and/or rootstock. The plant, plant part, plant cell, seed, and/or rootstock may be homozygous or heterozygous for the modified endogenous WRKY32 gene or protein.

In a preferred embodiment, the plant, plant part, plant cell, seed, and/or rootstock may be or may be from any plant species from the *Solanum* genus. In a further preferred embodiment, the plant, plant part, plant cell, seed, and/or rootstock as taught herein may be or may be from a tomato plant, more preferably a *Solanum lycopersicum* plant.

In an embodiment, the plant is a chimer plant comprising a rootstock that comprises an impaired or modified WRKY32 polynucleotide and/or WRKY32 polypeptide as taught herein. Preferably said chimer further comprises a scion of any other plant, preferably a scion of a plant not showing the increased nematode resistance as defined herein, even more preferably a scion of a control plant as defined herein.

Tomato Plants Comprising a Modified Polynucleotide

In a further aspect, the present invention relates to a tomato plant, plant part, rootstock, seed or cell, wherein the expression of an endogenous polynucleotide encoding a polypeptide comprising an amino acid sequence having at least 80%, more preferably at least 90%, even more preferably at least 95%, most preferably at least 98% or 99% sequence identity with SEQ ID NO:1, 2, 3, 4, 5, 6, 7, or 8 is impaired. In a preferred embodiment, said polynucleotide encodes a polypeptide comprising an amino acid sequence having at least 80%, more preferably at least 90%, even more preferably at least 95%, most preferably at least 98% or 99% sequence identity with SEQ ID NO:1, 8.

In an embodiment, said polynucleotide comprises a nucleic acid sequence that has at least 80%, more preferably at least 90%, even more preferably at least 95%, most preferably at least 98% or 99% sequence identity with the nucleic acid sequence of SEQ ID NO:10 or 11 or the nucleic acid sequence of the Solyc07g005650 gene.

In an embodiment, at least one nucleotide has been inserted, deleted or substituted in said polynucleotide, preferably one or more point mutations have been introduced in said polynucleotide. It is understood that said insertion, deletion or substitution of at least one nucleotide or said point mutation(s) in said polynucleotide has a functional effect or is a functional mutation that can alter or block or inhibit or cause loss of function or production of said polynucleotide or related polypeptide (i.e. WRKY32).

In an embodiment relating to the tomato plant, plant part, rootstock, seed or cell as taught herein, the expression and/or activity of a polypeptide comprising an amino acid sequence having at least 80%, more preferably at least 90%, even more preferably at least 95%, most preferably at least 98% or 99% sequence identity with the amino acid sequence of SEQ ID NO:1, 2, 3, 4, 5, 6, 7, or 8 is impaired. In a preferred embodiment, said polypeptide comprising an amino acid sequence having at least 80%, more preferably at least 90%, even more preferably at least 95%, most preferably at least 98% or 99% sequence identity with the amino acid sequence of SEQ ID NO: 8.

In an embodiment, the expression and/or activity of said polypeptide and/or the expression of said polynucleotide is impaired in the roots, but not in the shoots to avoid affecting the shoots.

In an embodiment relating to the tomato plant, plant part, seed, rootstock, or cell as taught herein, the polypeptide is a transcription factor protein belonging to the WRKY32 family, and comprises two WRKY domains, and is capable of specifically binding to at least one W-box comprised on one or more genes or polynucleotides.

In a preferred embodiment, tomato plant, plant part, rootstock, seed, or cell as taught herein, is a *Solanum lycopersicum* plant, plant part, rootstock, seed or cell.

In an embodiment, the impairment of the expression and/or activity of the polypeptide or the impairment of the expression of the polynucleotide as taught herein does not alter the phenotype of the plant, seed or cell compared to a control plant with the exception of improved nematode resistance. For instance, growth, ability to germinate, yield, development, physical attributes, etc are not altered or changed.

In an embodiment, the tomato plant, or a plant derived from seed or cell thereof as taught herein exhibits improved nematode resistance, preferably improved root-knot nematode and/or cyst nematode resistance, compared to a control plant.

In an embodiment, the nematodes are selected from the genera *Meloidogyne*, *Heterodera* or *Globodera*, preferably *Meloidogyne incognita*, *Meloidogyne javanica*, and *Globodera rostochiensis*.

In a further aspect, the present invention relates to rootstock of the tomato plant as taught herein and use thereof for improving growth and development of a graft.

In a preferred embodiment, the plant, plant part, plant cell, seed, or rootstock as taught herein is not a transgenic plants, plant part, plant cell, seed, or rootstock, i.e. does not contain any transgenic means or no foreign gene or polynucleotide has been added to the genome of plant, plant part, plant cell, seed, or rootstock.

In an embodiment, the *Solanum lycopersicum* plant is a chimer plant comprising a *Solanum lycopersicum* rootstock that comprises an impaired or modified WRKY32 polynucleotide and/or WRKY32 polypeptide as taught herein. Preferably said chimer further comprises a scion of any other plant, preferably a scion of a *Solanum lycopersicum* plant, more preferably a scion of a *Solanum lycopersicum* plant not showing the increased nematode resistance as defined herein, even more preferably a scion of a control plant as defined herein.

Uses of the Invention

In a further aspect, the present invention relates to the use of a polynucleotide encoding a polypeptide comprising an amino acid sequence having at least 80%, more preferably at least 90%, even more preferably at least 95%, most preferably at least 98% or 99% sequence identity with the amino acid sequence of SEQ ID NO: 1, 2, 3, 4, 5, 6, 7, 8 or 15 for improving or increasing nematode resistance in a plant cell, plant part or plant.

In a preferred embodiment, said polypeptide may comprise an amino acid sequence having at least 80%, more preferably at least 90%, even more preferably at least 95%, most preferably at least 98% or 99% sequence identity with the amino acid sequence of SEQ ID NO:8.

In an embodiment, said polypeptide is a transcription factor protein of the WRKY32 family, and comprises two WRKY domains, and is capable of specifically binding to at least one W-box comprised on a gene or polynucleotide.

In an embodiment, said polynucleotide may comprise a nucleic acid sequence that has at least 80%, more preferably at least 90%, even more preferably at least 95%, most preferably at least 98% or 99% sequence identity with the nucleic acid sequence of SEQ ID NO:10 or 11 or the nucleic acid sequence of the Solyc07g005650 gene.

SEQUENCE LISTING

SEQ ID NO: 1 Solanaceae consensus WRKY32 protein sequence
SEQ ID NO: 2 Brassicaceae consensus WRKY32 protein sequence
SEQ ID NO: 3 Cucurbitaceae consensus WRKY32 protein sequence
SEQ ID NO: 4 Fabaceae consensus WRKY32 protein sequence
SEQ ID NO: 5 Rosaceae consensus WRKY32 protein sequence
SEQ ID NO: 6 Poaceae consensus WRKY32 protein sequence
SEQ ID NO: 7 *Solanum* consensus WRKY32 protein sequence
SEQ ID NO: 8 *Solanum lycopersicum* WRKY32 protein sequence
SEQ ID NO: 9 *Solanum* consensus WRKY32 coding nucleic acid sequence
SEQ ID NO: 10 *Solanum lycopersicum* WRKY32 genomic nucleic acid sequence
SEQ ID NO: 11 *Solanum lycopersicum* WRKY32 coding nucleic acid sequence
SEQ ID NO: 12 *Solanum lycopersicum* WRKY32 RNAi sequence
SEQ ID NO: 13 *Arabidopsis thaliana* WRKY32 genomic nucleic acid sequence
SEQ ID NO: 14 *Arabidopsis thaliana* coding nucleic acid sequence
SEQ ID NO: 15 *Arabidopsis thaliana* protein sequence

EXAMPLES

Example 1

Nematode Disease Assays in *Solanum lycopersicum*

In order to test nematode resistance in tomato (*S. lycopersicum*) plants, we investigated if impaired expression or alteration of the WRKY32 protein encoded by the Solyc07g005650 gene resulted in reduced disease symptoms by root-knot nematode infection.
Test Group
In order to test the effect of reduced expression of Solyc07g005650 gene on the ability of the nematode *M. incognita* to infest the tomato (*S. lycopersicum*) plants, an experiment was performed whereby *S. lycopersicum* roots were transfected with an RNAi vector construct designed to silence the Solyc07g005650 gene, the RNAi having the sequence CTGACATGCCAGTACCCAAAAAACGT-CATGGTCCACCGAGTGCACCTCTTATTGCTG CTACTGCCCCTGCTTCCGTAACCACTATG-CATGCTAACAAACCCGAACCCCTACAAC ATCAAAAATCGAC-CACACAATGGTCCGTGGACAAAGAAGGT-GAGTTGACTGGTGAG AAATTGGATGTTGGAG-GAGAAAAAGCAATGG (SEQ ID NO: 12). *Rhizobium rhizogenes*-mediated transfection of tomato roots was visually aided by the presence of DS-red (used as fluorescent marker) on the same plasmid.

Figure 1:
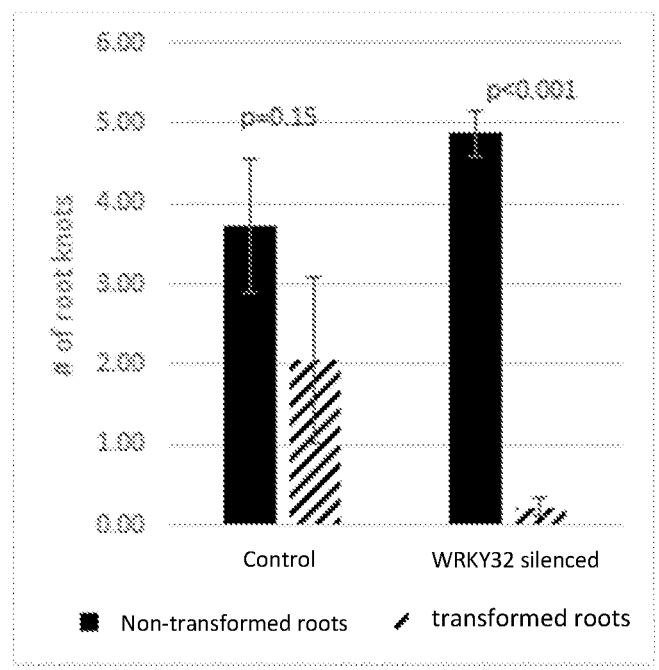
FIG. 1 shows the number of root knots on the roots caused by infection with *M. incognita* in plants wherein the expression of Solyc07g005650 gene was silenced compared to a control plant.

Control Group
The control group consisted of tomato (*S. lycopersicum*) plants, which were transformed with the vector construct but which was devoid of the RNAi designed to silence the Solyc07g005650 gene.
Following successful transfection with the vector construct as defined above, plants from both experimental groups (i.e. 3-week-old sand-grown tomato plants) were infected with 500 J2s of *M. incognita* per plant. Infection of tomato roots by *M. incognita* was determined 5 weeks post infection.
The number of root-knots caused by *M. incognita* was determined in both experimental groups (i.e. test and control groups). In the test group, roots, which were successfully transfected were identified by determining the presence of DS-red fluorescence in the roots using a binocular, see hatched bar in FIG. 1). Roots which were not successfully transfected in the test group plant did not show any DS-red fluorescent signal, see black bar In FIG. 1. Such roots served as an 'internal control' within the test group plants.
The number of root-knots formed was also determined in the control group plants i.e. plants that were transfected with the control vector (i.e. lacking RNAi designed to silence the Solyc07g005650 gene) using the same procedure as above. The results obtained for each experimental group were compared. The results are shown in FIG. 1.
FIG. 1 shows that in the test group (WRKY32 silenced), the roots that were successfully transfected (i.e., displayed DS-red fluorescent signal)) displayed about 90% fewer disease symptoms (root-knot) compared to the roots which were not transfected (i.e. displayed no DS-red fluorescent signal). Further, it was be observed that the (number of root-knots formed on the non-transfected roots in the test group was similar to that of the control group plants (i.e. both transfected and non-transfected roots). Moreover, it was observed that the plants of the test group displayed improved or greater nematode resistance than the plant of the control group (see hatched bar in FIG. 1).
In the control group, there was no significant difference in the number of root-knots on the transfected roots and non-transfected roots.
Overall, these results indicate that impairing (i.e. by silencing) the expression of the endogenous WRKY32 gene (Solyc07g005650 gene) in tomato (*S. lycopersicum*) plants causes increased or improved resistance to nematodes compared to control plants.

Example 2

Root-Knot Nematode Disease Assays in *Arabidopsis thaliana*
In order to test nematode resistance in *Arabidopsis* (*A. thaliana*) plants we investigated if impaired expression or alteration of the WRKY32 protein encoded by At4g30935 gene resulted in reduced disease symptoms by root-knot nematode (*Meloidogyne incognita*) infection.
Test Group
In order to assess the effect of impaired expression of At4g30935 gene (SEQ ID NO: 13 represents the genomic sequence; SEQ ID NO: 14 represents the coding sequence; SEQ ID NO: 15 represents the protein), on the ability of the nematode *Meloidogyne incognita* to infest *A. thaliana* plants, an experiment was performed whereby 10-days old plants of *A. thaliana* mutant line (SALK091352; Alonso et al, 2003, Science) containing T-DNA insertion in At4g30935 gene grown on sterile MS20/Gelrite medium in 6-well cell culture plates, were challenged with 200 sterile *Meloidogyne incognita* infective juveniles (J2s) per plant.

Control Group

The control group consisted of *A. thaliana* Col-0 wild type plants, ecotype that was used as a background to create a publicly available genome-wide collection of insertional mutants (Alonso et al, 2003, Science). Ten-days old plants grown on sterile MS20/Gelrite medium in 6-well cell culture plates, were challenged with 200 sterile *Meloidogyne incognita* infective juveniles (J2s) per plant.

Figure 2:
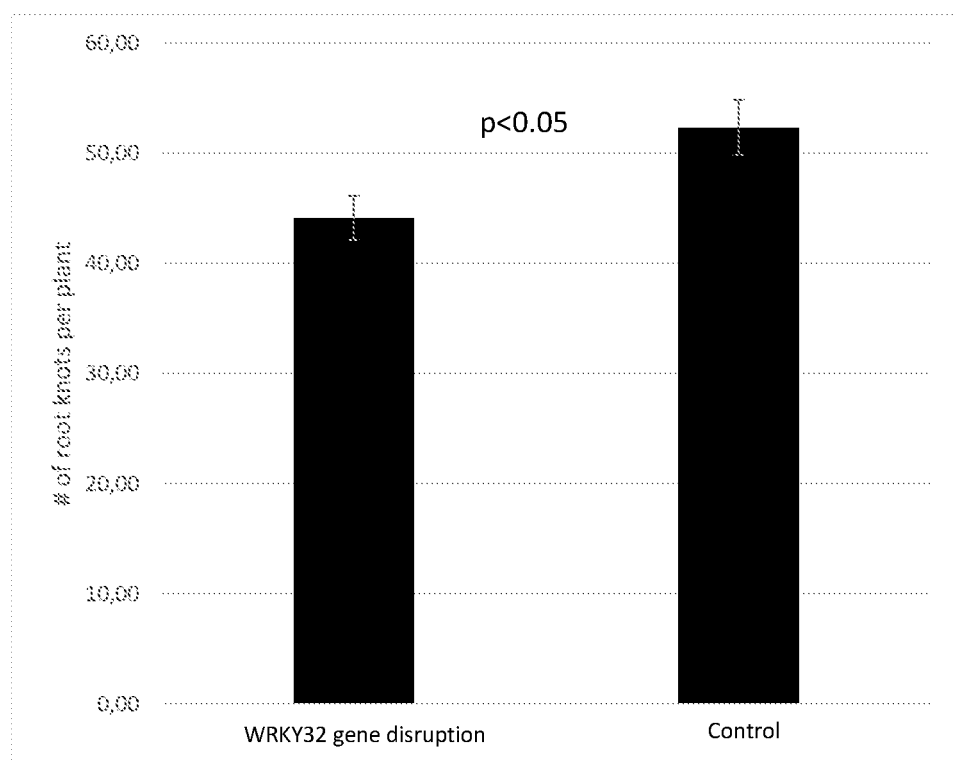
FIG. 2 shows the number of root knots on the roots caused by infection of *M. incognita* in *Arabidopsis* plants wherein the wrky32 gene was disrupted compared to a control plants.

The total number of root-knots caused by *M. incognita* was determined per plant in both experimental groups (i.e. test and control group) 5 weeks after inoculation with nematodes. FIG. 2 shows that in the test group (WRKY32 gene disruption) the roots displayed on average about 15% fewer root-knots compared to the roots of control group (Control). Further it was observed that the sizes of the root systems in the test group were similar to the root system sizes in the control roots.

Overall, these results indicate that knocking-out the expression of the At4g30935 gene in *Arabidopsis thaliana* caused improved resistance to root-knot nematodes compared to control plants.

Example 3

Beet-Cyst Nematode Disease Assays in *Arabidopsis thaliana*

In order to test nematode resistance in *Arabidopsis* (*A. thaliana*) plants we investigated if impaired expression or alteration of the WRKY32 protein encoded by At4g30935 gene resulted in reduced disease symptoms by beet cyst nematode (*Heterodera schachtii*) infection.

Test Group

In order to assess the effect of impaired expression of At4g30935 gene on ability of the nematode *Heterodera schachtii* to infest *A. thaliana* plants, an experiment was performed whereby 10-days old plants of *A. thaliana* mutant line (SALK_091352; Alonso et al, 2003, Science) containing T-DNA insertion in At4g30935 gene, grown on sterile KNOP/Daichin agar medium in 6-well cell culture plates, were challenged with 150 sterile *H. schachtii* infective juveniles (J2s) per plant.

Control Group

The control group consisted of *A. thaliana* Col-0 wild type plants, ecotype that was used as a background to create a publicly available genome-wide collection of insertional mutants (Alonso et al, 2003, Science). Ten-days old plants grown on sterile KNOP/Daichin agar medium in 6-well cell culture plates, were challenged with 150 sterile *H. schachtii* (IRS) infective juveniles (J2s) per plant.

Figure 3:
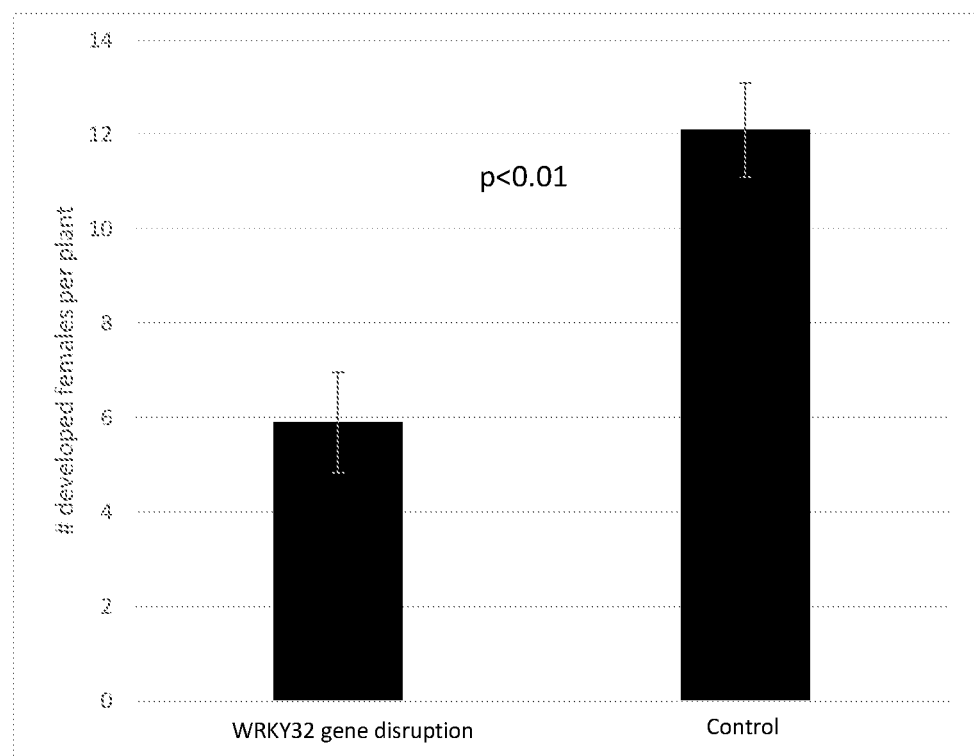
FIG. 3 shows the number of developed females per plant caused by *Heterodera schachtii* infection in *Arabidopsis* plants wherein the wrky32 gene was disrupted compared to a control plants.

The total number of developing *H. schachtii* females was determined per plant in both experimental groups (i.e. test and control group) 2 weeks after inoculation with nematodes. FIG. 3 shows that in the test group (WRKY32 gene disruption) the roots support development of on average about 51% fewer females compared to the roots of control group (Control). Further it was observed that the sizes of the root systems in the test group were similar to the root system sizes in the control roots.

Overall, these results indicate that knocking-out the expression of the At4g30935 gene in *Arabidopsis thaliana* caused improved resistance to beet cyst nematode compared to control plants.

The invention claimed is:

1. A method for producing a plant having improved nematode resistance compared to a control plant, comprising impairing in the plant at least one of
   (i) the expression and/or the activity of an endogenous WRKY32 polypeptide; and
   (ii) the expression of an endogenous WRKY32 polynucleotide encoding the WRKY32 polypeptide, wherein the expression and/or activity of the WRKY32 polypeptide and/or expression of the WRKY32 polynucleotide is impaired by at least one of modification of an endogenous WRKY32 gene and gene silencing targeting the WRKY32 polynucleotide, wherein the endogenous WRKY32 gene comprises a WRKY32 coding sequence operably linked to one or more regulatory elements, and wherein the produced plant is not an *Arabidopsis thaliana* plant comprising a T-DNA insertion in AT5G24910.

2. The method according to claim 1, wherein the WRKY32 polypeptide is a polypeptide comprising an amino acid sequence having at least 80% sequence identity to the amino acid sequence of any one of SEQ ID NO: 1, 2, 3, 4, 5, 6, 7, 8 and 15, and/or wherein the WRKY32 polynucleotide has at least 80% sequence identity with the nucleotide sequence of any one of SEQ ID NO: 9, 10, 11, 13 and 14.

3. The method according to claim 1, wherein the method further comprises the step of regenerating said plant.

4. The method according to claim 1, wherein the expression of said polypeptide and/or polynucleotide is impaired in at least the roots of said plant.

5. The method according to claim 1, wherein at least one of i) the expression and/or activity of the WRKY32 polypeptide; and ii) the expression of the WRKY32 polynucleotide is impaired by modifying the WRKY32 polynucleotide.

6. The method according to claim 5, wherein the modification of the WRKY32 polynucleotide comprises an insertion, a deletion or a substitution of at least one nucleotide in the polynucleotide.

7. A method according to claim 1, wherein the expression and/or activity of the WRKY32 polypeptide and/or expression of the WRKY32 polynucleotide is impaired using gene knock out.

8. A plant or rootstock having improved nematode resistance, or seed, plant part, or cell thereof, wherein expression and/or activity of an endogenous WRKY32 polypeptide and/or expression of an endogenous WRKY32 polynucleotide is impaired, wherein the expression and/or activity of the WRKY32 polypeptide and/or expression of the WRKY32 polynucleotide is impaired by at least one of modification of an endogenous WRKY32 gene and gene silencing targeting the WRKY32 polynucleotide, wherein the endogenous WRKY32 gene comprises a WRKY32 coding sequence operably linked to one or more regulatory elements, and wherein the plant, plant part, rootstock, seed or cell is not an *Arabidopsis thaliana* plant, plant part, rootstock, seed or cell comprising a T-DNA insertion in AT5G24910.

9. The plant or rootstock having improved nematode resistance, or seed, plant part, or cell thereof according to claim 8, wherein the WRKY32 polypeptide is a polypeptide comprising an amino acid sequence having at least 80% sequence identity to the amino acid sequence of any one of SEQ ID NO: 1, 2, 3, 4, 5, 6, 7, 8 and 15, and/or wherein the WRKY32 polynucleotide has at least 80% sequence identity with the nucleotide sequence of any one of SEQ ID NO: 9, 10, 11, 13 and 14.

10. A plant or rootstock having improved nematode resistance, or seed, plant part, or cell thereof, obtained by the method of claim 1, wherein the plant or rootstock having improved nematode resistance, or seed, plant part, or cell thereof has an impaired expression and/or activity of a WRKY32 polypeptide and/or an impaired expression of a WRKY32 polynucleotide.

11. The plant or rootstock having improved nematode resistance, or seed, plant part, or cell thereof according to claim 8, comprising a modified WRKY32 polynucleotide.

12. The plant or rootstock having improved nematode resistance, or seed, plant part, or cell thereof according to claim 11, wherein said modification comprises the insertion, deletion or substitution of at least one nucleotide in said polynucleotide.

13. The plant or rootstock having improved nematode resistance, or seed, plant part, or cell thereof according to claim 8, wherein expression and/or activity of the WRKY32 polypeptide and/or expression of the WRKY32 polynucleotide is impaired by gene silencing targeting the WRKY32 polynucleotide or gene knock out.

14. A progeny of the plant according to claim 8, wherein the progeny has an impaired expression and/or activity of a WRKY32 polypeptide and/or an impaired expression of a WRKY32 polynucleotide, wherein said progeny of the plant has improved nematode resistance.

\* \* \* \* \*